United States Patent
Popovic et al.

(10) Patent No.: US 10,980,607 B2
(45) Date of Patent: Apr. 20, 2021

(54) IMAGE GUIDANCE OF A STEERABLE INTRODUCER FOR MINIMALLY INVASIVE PROCEDURES

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 156 days.

(21) Appl. No.: 16/088,718

(22) PCT Filed: Mar. 28, 2017

(86) PCT No.: PCT/EP2017/057324
§ 371 (c)(1),
(2) Date: Sep. 26, 2018

(87) PCT Pub. No.: WO2017/167759
PCT Pub. Date: Oct. 5, 2017

(65) Prior Publication Data
US 2019/0110848 A1 Apr. 18, 2019

Related U.S. Application Data

(60) Provisional application No. 62/315,770, filed on Mar. 31, 2016.

(51) Int. Cl.
*A61B 34/00* (2016.01)
*A61F 2/24* (2006.01)
(Continued)

(52) U.S. Cl.
CPC ............ *A61B 34/74* (2016.02); *A61F 2/2427* (2013.01); *A61F 2/2466* (2013.01);
(Continued)

(58) Field of Classification Search
CPC ....... A61B 34/74; A61F 2/2427; A61F 2/2466
See application file for complete search history.

(56) References Cited

U.S. PATENT DOCUMENTS

| 8,764,820 B2 | 7/2014 | Dehdashtian |
| 9,984,437 B2 | 5/2018 | Thienphrapa |
| (Continued) | | |

FOREIGN PATENT DOCUMENTS

| EP | 2033593 A1 | 3/2009 |
| EP | 2561821 A1 | 2/2013 |
| (Continued) | | |

*Primary Examiner* — Richard G Louis

(57) ABSTRACT

A steerable introduction system for deploying an interventional tool (e.g., a replacement valve) within an anatomical object (e.g. a heart). The steerable introduction system employs a steerable introducer (20) including an end-effector for positioning the interventional tool within the anatomical object (e.g., the end-effector passively guides or actively steers the interventional tool within the anatomical object). The steerable introduction system further employs an image guidance workstation (120) controlling an actuation of a translation, a pivoting and/or a rotation of the end-effector within the anatomical object responsive to surgical image data illustrative of a position of the end-effector within the anatomical object (e.g., ultrasound or X-ray image data illustrative of a surgical position of the end-effector within a heart). The motion actuation by the image guidance workstation (120) of the end-effector facilitates a coaxial alignment and/or a coplanar alignment of the interventional tool and a structure of the anatomical object (e.g., a diseased aortic valve of a heart).

20 Claims, 19 Drawing Sheets

(51) Int. Cl.
   *A61B 90/00* (2016.01)
   *A61B 34/30* (2016.01)
   *A61B 34/20* (2016.01)

(52) U.S. Cl.
   CPC . *A61B 2034/2065* (2016.02); *A61B 2034/302* (2016.02); *A61B 2034/304* (2016.02); *A61B 2090/376* (2016.02); *A61B 2090/3782* (2016.02)

(56) References Cited

U.S. PATENT DOCUMENTS

2008/0287741 A1* 11/2008 Ostrovsky ............ A61B 1/0057
  600/141
2009/0171271 A1* 7/2009 Webster ............ A61M 25/0108
  604/95.01

FOREIGN PATENT DOCUMENTS

WO  2007059233 A2  5/2007
WO  2009148317 A1  12/2009

* cited by examiner

IMAGE GUIDANCE OF A STEERABLE INTRODUCER FOR MINIMALLY INVASIVE PROCEDURES

CROSS-REFERENCE TO PRIOR APPLICATIONS

This application is the U.S. National Phase application under 35 U.S.C. § 371 of International Application No. PCT/EP2017/057324, filed on Mar. 28, 2017, which claims the benefit of U.S. Provisional Patent Application No. 62/315,770, filed on Mar. 31, 2016. These applications are hereby incorporated by reference herein.

FIELD OF THE INVENTION

The present disclosure generally relates to a steerable introducer for deploying an interventional tool during a minimally invasive procedure of any type (e.g., a minimally invasive surgical valve replacement). The present disclosure specifically relates to novel and inventive steerable introducers for deploying interventional tools.

BACKGROUND OF THE INVENTION

An aortic valve replacement is a medical procedure in which a diseased aortic valve is replaced with an artificial valve. More particularly, a minimally invasive aortic valve replacement generally involves, under image X-ray or ultrasound guidance, a deployment of the artificial valve in a beating heart via a small incision in the patient's body.

There are numerous approaches for executing a minimally invasive aortic valve replacement.

A first example is a transapical approach generally involving a small incision in a lower part of a chest of a patient, and a small puncture in a left ventricle of a beating heart of the patient. An introducer sheath is guided through the small incision and small puncture into the left ventricle via a guidewire, and a balloon catheter supporting the artificial valve is introduced via the introducer sheath into the left ventricle for deploying the artificial valve at the diseased aortic valve site.

A second example is a transaortic approach generally involving a small incision in an upper part of a chest of a patient, and a small puncture in an aorta of a beating heart of the patient. An introducer sheath is guided through the small incision and small puncture into the aorta via a guidewire, and a balloon catheter supporting the artificial valve is introduced via the introducer sheath into the aorta for deploying the artificial valve at the diseased aortic valve site.

For a successful aortic valve replacement, the introduction of the balloon catheter in the left ventricle or the aorta requires both a coaxial alignment and a coplanar alignment of the artificial valve and the diseased aortic valve. However, both a coaxial alignment and a coplanar alignment of the artificial valve and the diseased aortic valve has proven to be challenging for various reasons due to the complex motion of the heart (e.g., heart beating and a flapping of the diseased aortic valve).

One primary reason is that the patient incision point, the heart puncture point and the aorta valve annulus are rarely co-linear, and therefore a straight line introduction of the balloon catheter into the left ventricle or the aorta is not suitable.

To address this straight line limitation of a straight-line introducer sheaths, introducer sheaths as known in the art have been equipped with deflection tendons to actuate a pitch motion and/or a yaw motion of a distal end of the introducer sheath with an aim to achieve the coaxial alignment and the coplanar alignment of the artificial valve and the diseased aortic valve.

However, a transmission length of the deflection tendons extends from the distal end to the proximal end of the introducer sheath and typically fails to provide a precise actuation of a desired pitch motion and/or yaw motion of the distal end of the introducer sheath for the coaxial alignment and the coplanar alignment of the artificial valve and the diseased aortic valve, particularly in view of anatomical structures of the patient (e.g., ribs, hear muscles, trabeculations inside the heart) limiting such actuation of the introducer sheath.

Furthermore, the deflection tendons do not provide a translational motion of the introducer sheath that may be necessary for both the coaxial alignment and the coplanar alignment of the artificial valve and the diseased aortic valve.

SUMMARY OF THE INVENTION

The inventions of the present disclosure improve upon steerable introducers by providing an image guidance of the steerable introducer(s) within an anatomical object to thereby achieve a precise coaxial alignment and/or a precise coplanar alignment of ah interventional tool with a structure of the anatomical object (i.e., any anatomical organ and any blood vessel).

For purposes of the inventions of the present disclosure, the terms "minimally invasive procedure" and "interventional tool" are to be broadly interpreted as understood in the art of the present disclosure and as exemplary described herein.

Examples of a minimally invasive procedure include, but are not limited to, heart valve procedures (aortic, pulmonary, mitral) repair and replacement, atrial septal defect or patent foramen ovale closures, retrieval of foreign bodies or clots from the heart, vascular procedures, video-assisted thoracic surgery and abdominal surgery (liver, kidney, prostate).

Examples of an interventional tool include, but are not limited to, artificial heart devices, closure devices, suction devices, punches, catheters, balloon catheters, ablation catheters, stents and grafts.

For purposes of the inventions of the present disclosure, the term "steerable introducer" broadly encompasses all structural configurations of introducer sheaths, surgical introducers and the like as known in the art that incorporate a steerable actuation of an end-effector for passively guiding or actively steering a positioning of an interventional tool within an anatomical object as understood in the art of the present disclosure and as exemplary described herein, and the term "steerable introduction device" broadly encompasses a combination of two (2) or more steerable introducers in a stacked arrangement as understood in the art of the present disclosure and as exemplary described herein.

One form of the inventions of the present disclosure is a steerable introduction system for deploying an interventional tool (e.g., a replacement valve) within an anatomical object (e.g. a heart) with the steerable introduction system employing a steerable introducer including an end-effector for positioning the interventional tool within the anatomical object (e.g., the end-effector passively guides or actively steers the interventional tool within the anatomical object).

The steerable introduction system further employs an image guidance workstation controlling an actuation of a translation, a pivoting and/or a rotation of the end-effector within the anatomical object responsive to surgical image data illustrative of a position of the end-effector within the anatomical object (e.g., ultrasound or X-ray image data illustrative of a surgical position of the end-effector within a heart).

The motion actuation by the image guidance workstation of the end-effector facilitates a coaxial alignment and/or a coplanar alignment of the interventional tool and a structure of the anatomical object (e.g., a diseased aortic valve of a heart).

For the first form of the steerable introduction system, the steerable introducer may employ a motion coupler coupling a shaft and the end-effector.

The shaft is structurally configured to introduce the interventional tool into the anatomical object (e.g., the interventional tool passes through or over the shaft into the anatomical object). The end-effector is structurally configured to interact with the interventional tool within the anatomical object (e.g., the end-effector is movable to position the interventional tool within the anatomical object).

The motion coupler includes one or more linear actuators controllable to actuate a translation, a pivoting and/or a rotation of the end-effector relative to the shaft. An actuation of the linear actuator(s) provides a translational motion, a pitch motion and/or a yaw motion of the end-effector to achieve a coaxial alignment and/or a coplanar alignment of the interventional tool with a structure of the anatomical object (e.g., a coaxial alignment and/or coplanar alignment of the artificial valve to a diseased aortic valve of a heart).

The motion coupler may further include one or more linear sliders translatable between the shaft and the end-effector, and/or one or more post extending between the shaft and the end-effector. If included, the linear slider(s) and/or the post(s) support the translation, pivoting and/or a rotation of the end-effector within the anatomical object responsive to an actuation of the linear actuator(s).

The motion coupler may further includes a rotary actuator controllable to actuate a rotation of the end-effector about a rotational axis of the end-effector and/or the steerable introducer further employs a rotary actuator controllable to actuate a rotation of the end-effector about a rotational axis of the shaft. An actuation of the rotary actuator(s) provides a roll motion of the end-effector and/or a revolution motion of the end-effector about the shaft to further achieve the coaxial alignment and/or the coplanar alignment of the interventional tool with the structure of the anatomical object.

For purposes of the inventions of the present disclosure, the structural terms "shaft" and "end-effector" are to be broadly interpreted as understood in the art of the present disclosure and as exemplary described herein.

For purposes of the inventions of the present disclosure, the structural term "motion coupler" broadly encompasses all structural configurations of a coupler actuatable to apply one or more moving force(s) (e.g., linear and/or angular) to a body connected to the coupler (e.g., an end-effector).

For purposes of the inventions of the present disclosure, the structural terms "linear actuator", "linear slider", "post" and "rotational actuator" are to be broadly interpreted as understood in the art of the present disclosure and as exemplary described herein.

A non-limiting example of a linear actuator is motorized prismatic joint incorporating a piezoelectric motor or a pneumatic motor.

A non-limiting example of a linear slider is a non-motorized prismatic joint incorporating a pneumatic slider.

A non-liming example of a post is a fulcrum about which an end-effector pivots and/or rotates.

A non-limiting example of a rotational actuator is a motorized rotary joint incorporating a piezoelectric motor.

For purposes of the inventions of the present disclosure, the descriptive terms "introduce", "interact", "actuate", "translate", "pivot", "rotate", "pitch", "yaw", "roll", "revolve", "coaxial", "coplanar", "alignment" and "axis", and any tenses thereof are to be broadly interpreted as understood in the art of the present disclosure and as exemplary described herein.

More particularly, the term "interact" as related to the end-effector and the interventional device broadly encompasses end-effector affecting a physical disposition of the interventional device within the anatomical object. One non-limiting example is the end-effector guiding a positioning of the interventional device within the anatomical object in terms of location and/or orientation. Another non-limiting example is the end-effector steering a positioning of the interventional device within the anatomical object in terms of location and/or orientation.

A second form of the inventions of the present disclosure is a steerable introduction system for deploying an interventional tool (e.g., a replacement valve) within an anatomical object (e.g. a heart) with the steerable introduction system employing a steerable introduction device including an orienting end-effector and a translating end-effector for positioning the interventional tool within the anatomical object.

The steerable introduction system further employs an image guidance workstation controlling an actuation of a pivoting and/or a rotation of the orienting end-effector within the anatomical object responsive to surgical image data illustrative of a surgical orientation of the translating end-effector within the anatomical object, and further controlling an actuation of a translation of the translating end-effector within the anatomical object responsive to surgical image data illustrative of a surgical location of the translating end-effector within the anatomical object.

The motion actuation by the image guidance workstation of the orienting end-effector and the translating end-effector facilitates a coaxial alignment and/or a coplanar alignment of the interventional tool and a structure of the anatomical object (e.g., a diseased aortic valve of a heart).

For the second form of the steerable introduction system, the steerable introducer may employ an orienting steerable introducer and a translating steerable introducer with a shaft of the translating steerable introducer being adjoined to an end-effector of the orienting steerable introducer. A motion coupler of the orienting steerable introducer includes one or more linear actuators controllable to actuate a pivoting and/or a rotation of the end-effectors of the steerable introducers relative to a shaft of the orienting steerable introducer. A motion coupler of the translating steerable introducer includes one or more linear actuators controllable to actuate a translation of the end-effector of the translating steerable introducer relative to a shaft of the translating steerable introducer.

For purposes of inventions of the present disclosure, the term "adjoined" and any tense thereof broadly encompasses a secure or a separable coupling, connection, affixation, clamping, mounting, etc. of components.

For purposes of the present disclosure, the labels "orienting" and "translating" used herein for the term "steerable introducer" and components thereof distinguishes for identification purposes a particular steerable introducer and components thereof from other steerable introducers as described and claimed herein without specifying or implying any additional limitation to the term "steerable introducers".

For both forms of the steerable introduction systems, the image guidance workstation may employ a control network including an image controller, an introducer controller and application modules as exemplary described herein.

For purposes of the inventions of the present disclosure, the term "workstation" is to be broadly interpreted as understood in the art of the present disclosure and as exemplary described herein. Examples of a "workstation" include, but are not limited to, an assembly of one or more computing devices, a display/monitor, and one or more input devices (e.g., a keyboard, joysticks and mouse) in the form of a standalone computing system, a client computer, a desktop or a tablet.

For purposes of the present disclosure, the term "controller" broadly encompasses all structural configurations of an application specific main board or an application specific integrated circuit housed within or linked to a workstation for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s).

For purposes of the present disclosure, the labels "introducer", "motor", "image", "X-ray" and "ultrasound" used herein for the term "controller" distinguishes for identification purposes a particular controller from other controllers as described and claimed herein without specifying or implying any additional limitation to the term "controller".

For purposes of the present disclosure, the term "application module" broadly encompasses a module incorporated within or accessible by a controller consisting of an electronic circuit and/or an executable program (e.g., executable software stored on non-transitory computer readable medium(s) and/firmware) for executing a specific application.

A third form of the inventions of the present disclosure is an interventional method incorporating a steerable introducer including an end-effector for positioning an interventional tool within an anatomical object. The interventional method involves a placement of the end-effector into the anatomical object.

The interventional method further involves the image guidance workstation steering the end-effector to a position within the anatomical object including the image guidance workstation controlling an actuation by of at least one of a translation, a pivoting and a rotation of the end-effector within the anatomical object responsive to surgical image data illustrative of a position of the end-effector within the anatomical object.

The foregoing forms and other forms of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

As an improvement upon prior deflectable introducer sheaths, the inventions of the present disclosure propose a steerable introducer employing one or more linear actuators for localizing necessary degree(s) of freedom of an end-effector to thereby achieve a precise coaxial alignment and/or a precise coplanar alignment of the interventional tool with a structure of an anatomical object (i.e., any anatomical organ and any blood vessel).

Figure 1A:
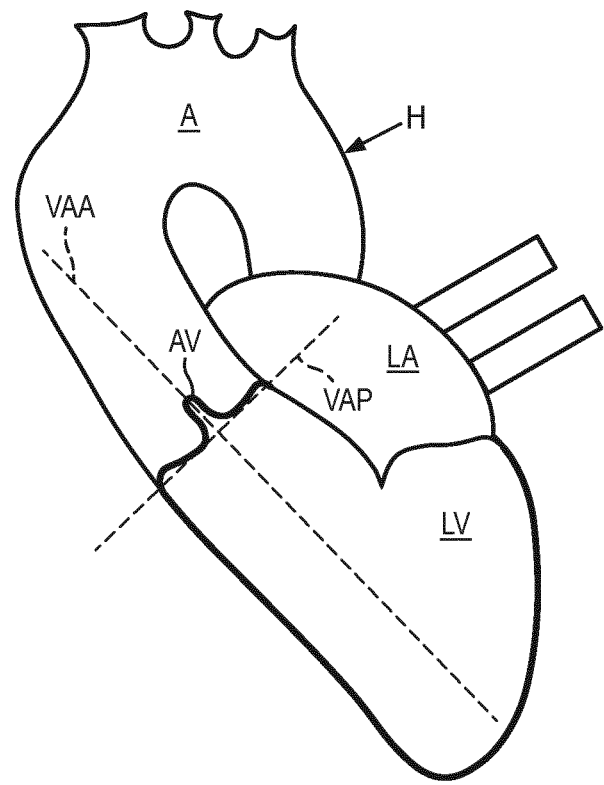
FIGS. 1A-1E illustrate an exemplary deployment of a replacement valve by a steerable introducer in accordance with the inventive principles of the present disclosure.

For example, an aorta A, a left atrium LA and a left ventricle LV of a beating heart H as shown in FIG. 1A are involved in a minimally invasive aortic valve replacement requiring a precise coaxial alignment of a replacement artificial valve with a valve annulus axis VAA of a diseased aortic valve AV and a precise coplanar alignment of the replacement artificial valve with a valve annulus plane VAP of the diseased aortic valve AV (or any other plane perpendicular to disease aortic valve as decided by a surgeon). A transapical approach of the minimally invasive surgical aortic valve replacement generally involves a small incision in a lower part of a chest (not shown), and a small puncture in left ventricle LV of the beating heart H. More particularly for this transapical approach, a straight line introduction of the replacement artificial valve into the left ventricle LV to the aortic valve AV does not exist, and space within the left ventricle LV adjacent the aortic valve AV is limited.

Figure 1B:
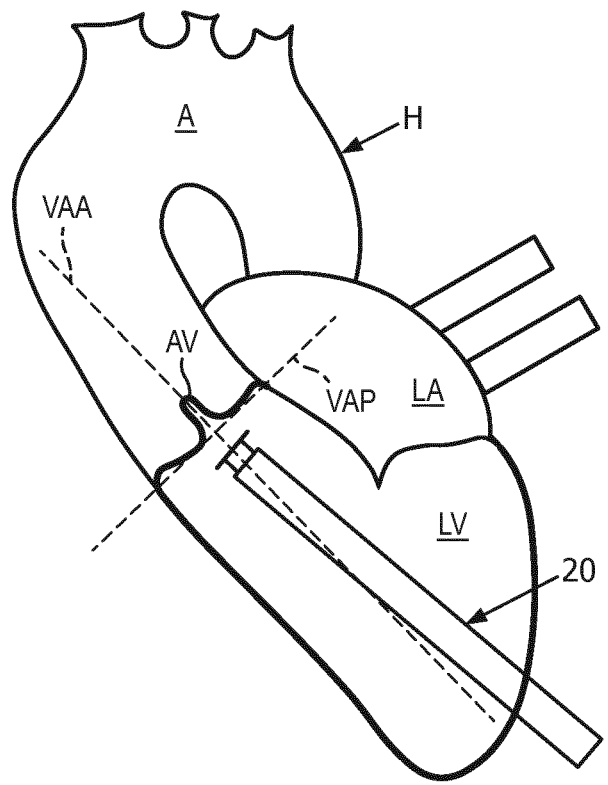

An execution of the transapical approach in accordance with the present disclosure may involve a steerable introducer 20 of the present disclosure guided through the small incision in the chest and small puncture into the left ventricle LV with or without a guidewire. A position of an end-effector of steerable introducer 20 is therefore misaligned with both the valve annulus axis VAA and the valve annulus plane VAP of the diseased aortic valve AV as shown in FIG. 1B.

Figure 1C:
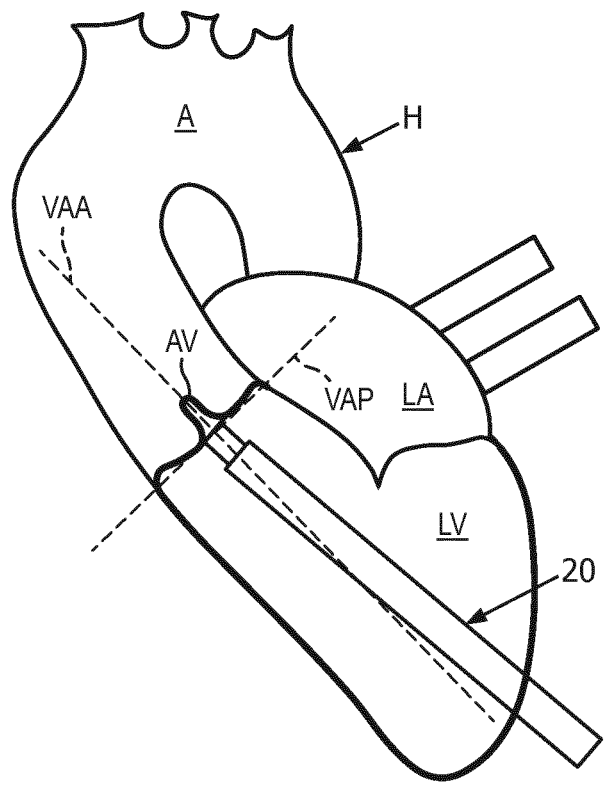
Figure 1D:
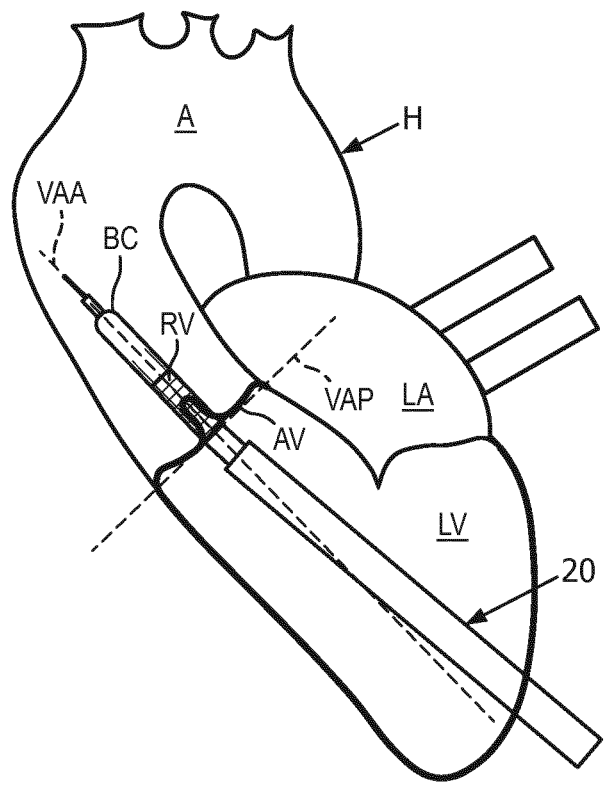
Figure 1E:
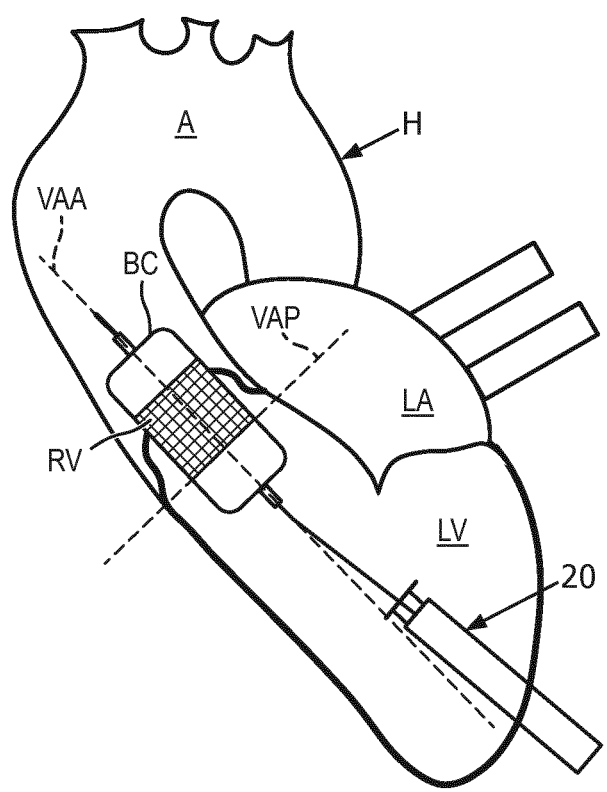

As will be further described herein, steerable introducer 20 of the present disclosure is actuatable to translate, pivot and/or rotate the end-effector of steerable introducer 20 as needed to position the end-effector in a precise coaxial alignment with the valve annulus axis VAA and in a precise coplanar alignment with the valve annulus plane VAP of the diseased aortic valve AV as shown in FIG. 1C. As such, a balloon catheter BC supporting a replacement artificial valve RV may be introduced via steerable introducer 20 of the present disclosure into the left ventricle LV as shown in FIG. 1D with a precise coaxially alignment of the replacement artificial valve RV with the valve annulus axis VAA of the diseased aortic valve AV and a precise coplanar alignment of the replacement artificial valve RV with the valve annulus plane VAP of the diseased aortic valve AV. The result is a proper deployment of the replacement artificial valve RV as illustrated in FIG. 1E.

Figure 2:
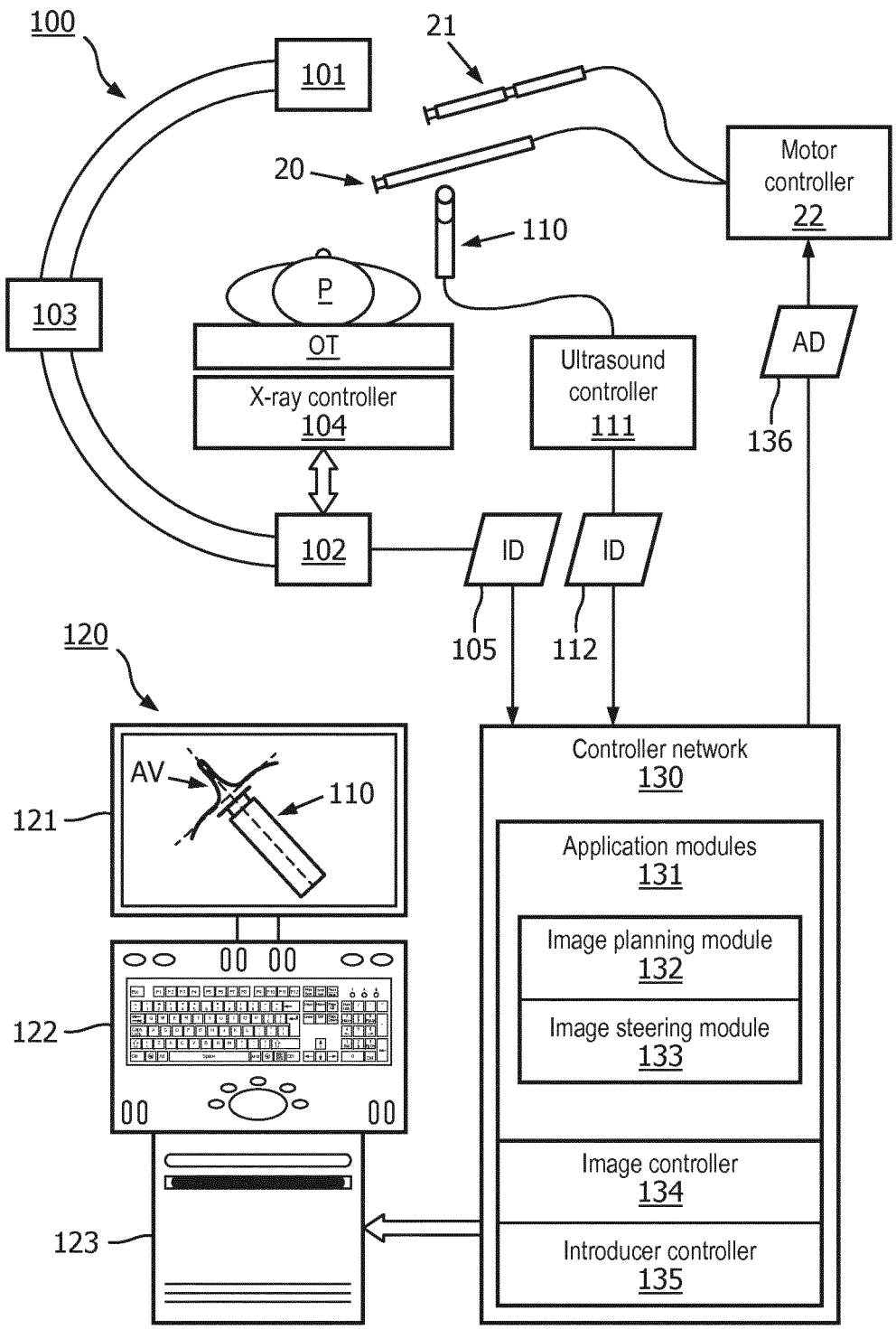
FIG. 2 illustrates an exemplary embodiment of an interventional system in accordance with the inventive principles of the present disclosure.

To facilitate an understanding of the various inventions of the present disclosure, the following description of FIG. 2 teaches basic inventive principles associated with interventional systems of the present disclosure. From this description, those having ordinary skill in the art will appreciate how to apply the inventive principles of the present disclosure for making and using additional embodiments of interventional systems of the present disclosure. Please note the components of the present disclosure as shown in FIG. 2 are not drawn to scale, but drawn to conceptually visualize the inventive principles of the present disclosure.

Referring to FIG. 2, an interventional system of the present disclosure employs steerable introducer 20 or a steerable introduction device 21, a motor controller 22, a fluoroscopic imager 100 (e.g., a mobile c-arm as shown) and/or an ultrasound probe 110, an image guidance workstation 120 and a control network 130 for deploying an interventional tool within an anatomical object of a patient P lying prone on an operating table OT during a minimally invasive procedure of any type.

As known in the art, fluoroscopic imager 100 generally includes an X-ray generator 101, an image intensifier 102 and a collar 103 for rotating fluoroscopic imager 100. In operation as known in the art, an X-ray controller 104 controls a generation by fluoroscopic imager 100 of imaging data 105 illustrative of a fluoroscopic image of the anatomical object of patient P (e.g., a heart of patient P during a minimally invasive aortic valve replacement).

In practice, X-ray controller 104 may be installed within an X-ray imaging workstation (not shown), or alternatively installed within image guidance workstation 120.

Ultrasound probe 110 is any type of probe suitable for a particular minimally invasive procedure (e.g., a Transesophageal echocardiography (TEE) probe for a minimally invasive aortic valve replacement as shown). In operation as known in the art, an ultrasound controller 111 controls a generation by ultrasound probe 110 of imaging data 112 illustrative of an ultrasound image of the anatomical object of patient P (e.g., a heart of patient P during a minimally invasive aortic valve replacement).

In practice, ultrasound controller 111 may be installed within an ultrasound imaging workstation (not shown), or alternatively installed within image guidance workstation 120.

Workstation 120 is assembled in a known arrangement of a standalone computing system employing a monitor 121, a keyboard 122 and a computer 123.

Control network 130 is installed on computer 123, and employs application modules 131 including an image planning module 132 and an image steering module 133. Control network 130 further includes an image controller 134 and an introducer controller 135.

Image controller 134 generally processes image data as known in the art for an illustration of the image on display 121. For example, image controller 134 may process X-ray image data 105 for an illustration of an X-ray image on display 121, and/or process ultrasound image data 112 for an illustration of an ultrasound image on display 121.

In support of the minimally invasive procedure, image controller 134 executes or accesses image planning module 132 to facilitate a user delineation of a coaxial alignment and/or a coplanar alignment of an interventional tool to a structure of anatomical object of patient P (e.g., an aortic valve AV of heart of patient P). To this end, image controller 134 controls an illustration of an X-ray image and/or an ultrasound image of the structure of the anatomical object on display 121, or concurrently or alternatively controls an illustration of a registered pre-operative image of the structure of the object on display 121 (e.g., a computed-tomography image or a magnetic resonance image). An operator of workstation 120 delineates, within the image(s), a target position of an end-effector of steerable introducer 20 or of steerable introduction device 21 for achieving a coaxial alignment and/or a coplanar alignment of the interventional tool to the structure of anatomical object of patient P within the displayed image(s).

For example, the operator of workstation 120 may delineate, within the image(s), a target position of an end-effector of steerable introducer 20 or of steerable introduction device 21 based on an intersection of valve annulus axis VAA and valve annulus plane VAP of a diseased aortic valve AV as shown in FIG. 1A.

During the minimally invasive procedure, image controller 134 executes or accesses image steering module 133 to identify an end-effector of steerable introducer 20 or steerable introduction device 21 within the displayed image(s) whereby introducer controller 135 may ascertain any necessary translational, pivot and/or rotation of the end-effector of steerable introducer 20 or steerable introduction device 21 necessary to reach the target position for achieving a coaxial alignment and/or a coplanar alignment of an interventional tool to the structure of the anatomical object of patient P.

For example, image controller 134 may identify, within the image(s), the end-effector of steerable introducer 20 or steerable introduction device 21 relative to the delineated valve annulus axis VAA and valve annulus plane VAP of a diseased aortic valve AV as shown in FIG. 1B whereby introducer controller 135 ascertains any necessary translational, pivot and/or rotation of the end-effector of steerable introducer 20 or steerable introduction device 21 necessary to reach the target position for achieving the coaxial alignment with valve annulus axis VAA and the coplanar alignment of valve annulus plane VAP as shown in FIG. 1C.

In practice, image steering module 133 is built to implement the kinematics of steerable introducer 20 or of steerable introduction device 21. By implementing the kinematic model as known in the art of steerable introducer 20 or steerable introduction device 21, an execution of image steering module 133 by introducer controller 135 enables introducer controller 135 to ascertain linear motion parameter(s) for linear actuator(s) of steerable introducer 20 or for linear actuator(s) of steerable introduction device 21 to reach the target position as will be further explained herein. Introducer controller 135 generates actuation data 126 informative of desired linear motion parameter(s) for the linear actuator(s) and communicates actuation data 126 to motor controller 22 for actuating a translation, pivot and/or rotation by the linear actuator(s) of the end-effector of steerable introducer 20 or the end-effector of steerable introduction device 21 to reach the target position for achieving a coaxial alignment and/or a coplanar alignment of the interventional tool to the structure of the anatomical object of patient P.

For example, the operator of workstation 120 may manipulate the user input device of workstation 120 to actuate a translational, pivot and/or rotation by the linear actuator(s) of the end-effector of steerable introducer 20 or steerable introduction device 21 necessary to reach the target position for achieving the coaxial alignment with valve annulus axis VAA and the coplanar alignment of valve annulus plane VAP as shown in FIG. 1C.

In practice, motor controller 22 may be a standalone controller or installed within image guidance workstation 120.

Figure 3:
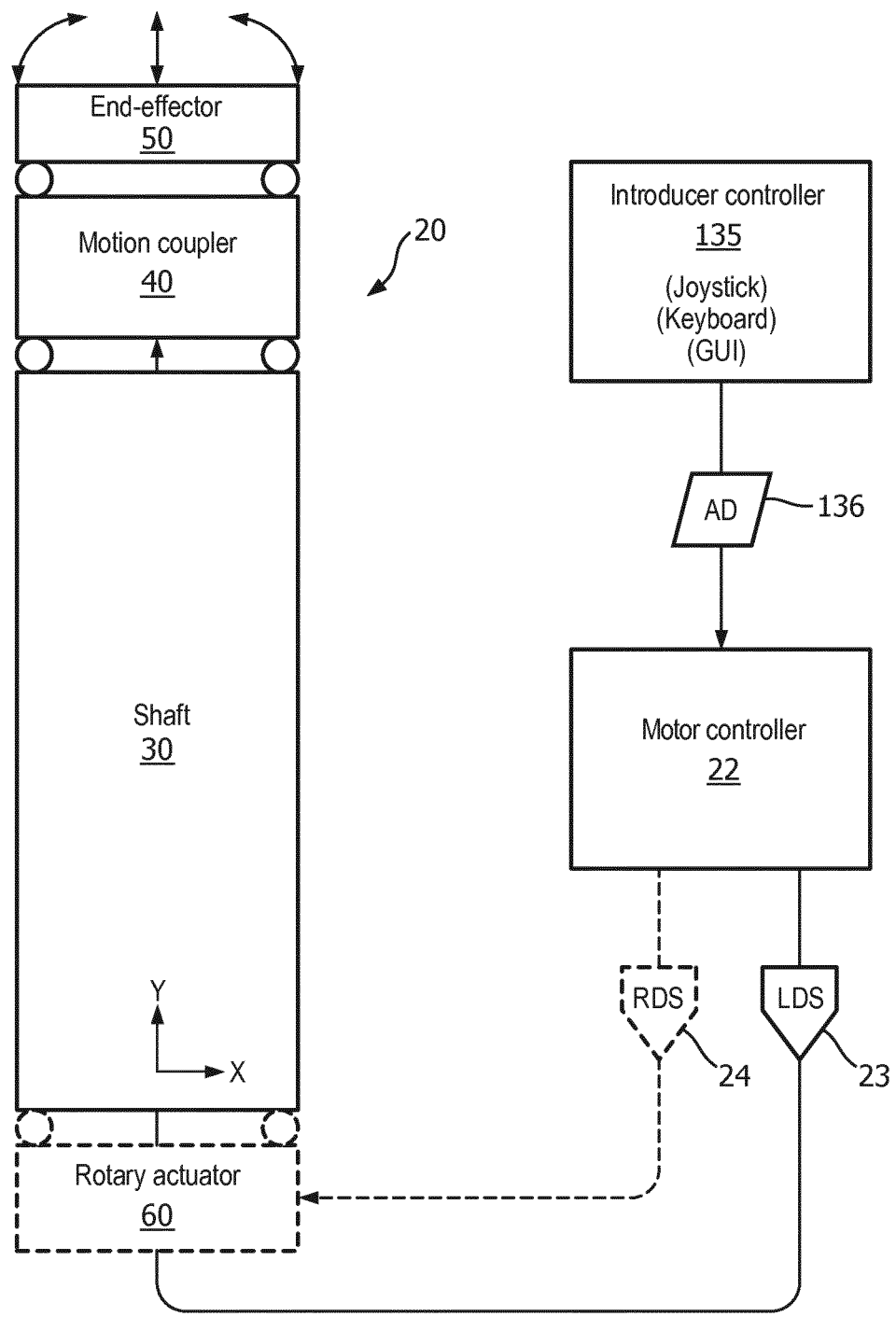
FIG. 3 illustrates an exemplary general embodiment steerable introducer in accordance with the inventive principles of the present disclosure.

To facilitate an understanding of the various inventions of the present disclosure, the following description of FIG. 3 teaches basic inventive principles of the present disclosure associated with a manufacture of a steerable introducer of the present disclosure. From this description, those having ordinary skill in the art will appreciate how to apply the inventive principles of the present disclosure for making numerous and various embodiments of steerable introducers of the present disclosure. Please note the components of the present disclosure as shown in FIG. 3 are not drawn to scale, but drawn to conceptually visualize the inventive principles of the present disclosure.

Referring to FIG. 3, a steerable introducer 20 of the present disclosure employs a shaft 30, a motion coupler 40, an end-effector 50 and an optional rotary actuator 60.

A structural configuration of shaft 30 is specified in terms of shape and dimensions to introduce an interventional tool into an anatomical object. In practice, as would be appreciated by those skilled in the art, a particular structural design and a particular material composition of shaft 30 is dependent upon particular minimally invasive procedure(s) utilizing steerable introducer 20.

In a first embodiment, as will be further described herein, shaft 30 is specified as a rigid or a semi-rigid shaft having a hollow central core for passing an interventional tool through shaft 30 to end-effector 50, and further having one or more lumens for passing electrical wiring through shaft 30 to motion coupler 40.

In a second embodiment, shaft 30 is specified as a rigid or a semi-rigid shaft having a solid central core for passing an interventional tool over shaft 30 to end-effector 50, and further having one or more lumens for passing electrical wiring through shaft 30 to motion coupler 40.

A structural configuration of end-effector 50 is specified in terms of shape and dimension for an interaction of end-effector 50 with the interventional tool as the interventional tool is being introduced by shaft 30 into the anatomical object. In practice, as would be appreciated by those skilled in the art, a particular structural design and a particular material composition of end-effector 50 is dependent upon particular minimally invasive procedure(s) utilizing steerable introducer 20.

In one embodiment, as would be appreciated by those skilled in the art, end-effector 50 is shaped and dimensioned as a cylinder for passively guiding or actively steering a positioning of the interventional tool within the anatomical object. For this embodiment, the interventional tool is passed through shaft 30 and end-effector 50 subsequent to a desired positioning of end-effector 50 within the anatomical object, or alternatively the interventional tool is passed through shaft 30 and adjoined to end-effector 50 prior to a placement of steerable introducer 20 into the anatomical object.

In another embodiment, as would be appreciated by those skilled in the art, end-effector 50 is shaped and dimensions as a plate for actively steering a positioning of the interventional tool within the anatomical object. For this embodiment, the interventional tool is passed through or over shaft 30 and adjoined to end-effector 50 prior to an placement of steerable introducer 20 into the anatomical object.

A structural configuration of motion coupler 40 is specified in terms of one or more linear actuator(s) (not shown) serving as motorized prismatic joint(s) coupling shaft 30 and end-effector 50 in a manner that facilitates a controllable actuation of the linear actuator(s) to translate, pivot and/or rotate end-effector 50 relative to shaft 30 as symbolized by the arrows extending from end-effector 50.

In one embodiment, as will be further described herein, a linear actuator includes a piezoelectric motor (not shown) coupled to shaft 30 for translating a rod (not shown) coupled to end-effector 50 in a forward direction or a reverse direction.

The structural configuration of motion coupler 40 may be further specified in terms of one or more linear slider(s) (not shown) serving as a non-motorized prismatic joint translatable between shaft 30 and end-effector 50 to facilitate a pivoting and/or rotation of end-effector 50 relative to shaft 30.

In one embodiment, as will be further described herein, a linear slider is a pneumatic slider including a non-translatable member (not shown) coupled to shaft 30 and a translatable member coupled to end-effector 50 whereby the translatable member is translatable in a forward direction or a reverse direction.

The structural configuration of motion coupler 40 may be further specified in terms of one or more posts (not shown) serving as a rigid joint coupled to shaft 30 and end-effector 50.

In one embodiment, as will be further described herein, a post is a fulcrum for enhancing a pivoting and/or rotation of end-effector 50 relative to shaft 30.

If employed, rotary actuator 60 is coupled to shaft 30 as shown in a manner that facilitates a controllable actuation of rotary actuator 60 to rotate shaft 30 about a rotational axis of shaft 30 (e.g., a longitudinal axis of shaft 30), or alternatively incorporated within motion controller 40 in a manner that facilitates a controllable actuation of rotary actuator 60 to rotate end-effector 50 about a rotational axis of end-effector 50 (e.g., a central axis of end-effector 50).

In operation as previously described herein, introducer controller 135 is responsive to a user input device (e.g., a joystick, a keyboard or a graphical user interface) for interpreting encoded emotion parameters of the user input device (e.g., translation, pitch and yaw motion parameters) into linear motion parameter(s) for the linear actuator(s), and if applicable, into a rotational motion parameter for rotary actuator 60. Introducer controller 135 generates actuation data 136 informative of a desired linear motion parameter(s) for the linear actuator(s) and if applicable of a desired rotational motion parameter for rotary actuator 60.

Actuation data 135 is communicated to a motor controller 22 that translates the desired linear motion parameter(s) into linear drive signal(s) 23 transmitted to one or more of the linear actuator(s) whereby each actuated linear actuator will apply a linear force to end-effector 50 in a forward direction or a reverse direction. As will be further described herein, the application of the linear force(s) actuates a translation, a pivoting or a rotation of end-effector 50 relative to shaft 30.

If applicable, motor controller 22 translates the desired rotational motion parameter into a rotational drive signal 24 transmitted to rotary actuator 60 whereby rotary actuator 60 will apply a rotational force to shaft 30 or end-effector 50 in a clockwise direction or a counterclockwise direction.

In practice, motor controller 22 may be external to steerable introducer 20 as shown, or alternatively as further described herein, each linear actuator 40 and rotary actuator 60 if applicable may employ an individual motor controller 22.

To facilitate an understanding of the various inventions of the present disclosure, the following description of FIGS. 4-9B teaches various embodiments of a steerable introducer of the present disclosure. From this description, those having ordinary skill in the art will appreciate how to apply the inventive principles of the present disclosure for using numerous and various embodiments of steerable introducers of the present disclosure. Please note the components of the present disclosure as shown in FIGS. 4-9B are not drawn to scale, but drawn to conceptually visualize the inventive principles of the present disclosure.

Figure 4:
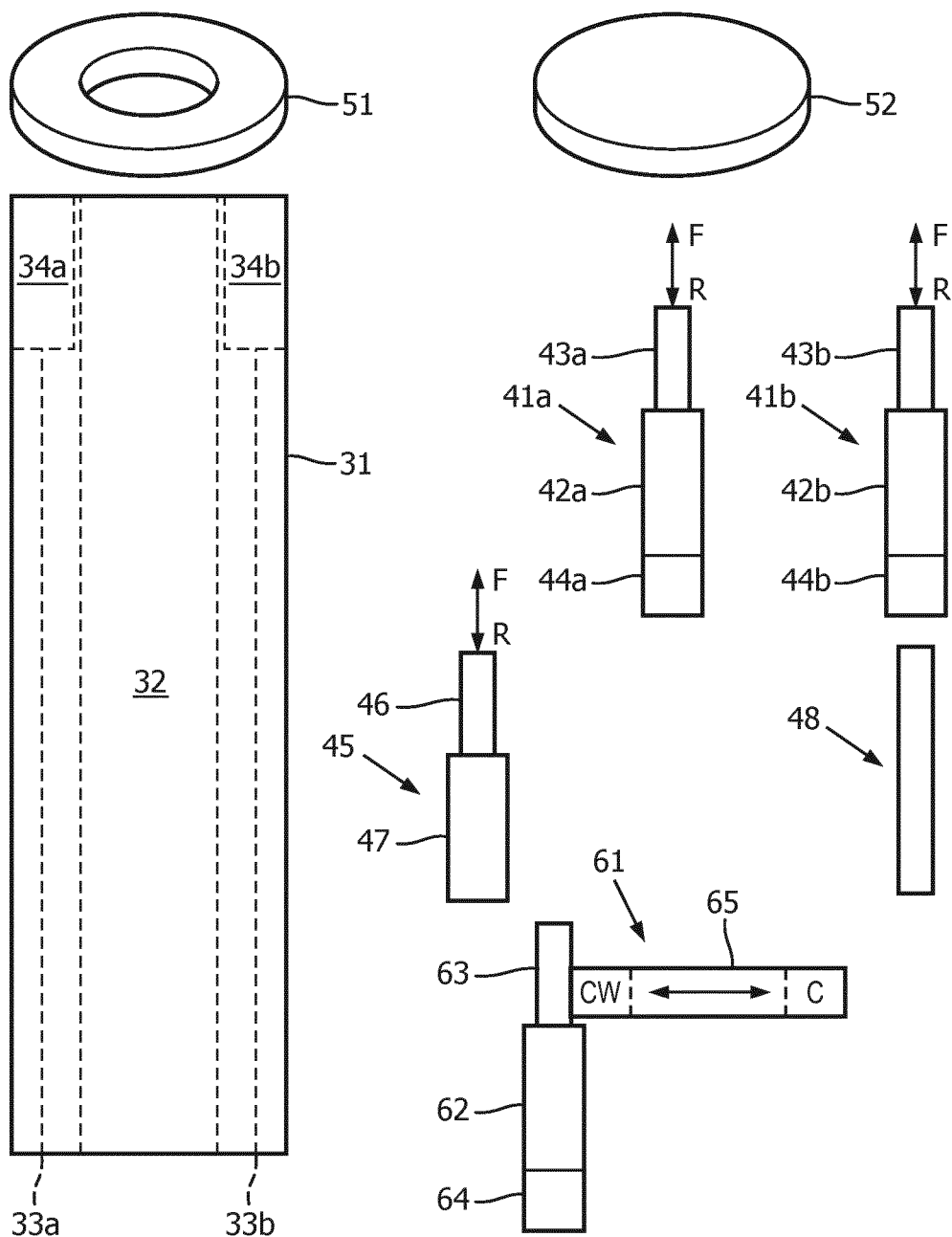
FIG. 4 illustrates an exemplary unassembled embodiment of the steerable introducer shown in FIG. 3 in accordance with the inventive principles of the present disclosure.

FIG. 4 shows an unassembled view of an embodiment of steerable introducer 20 (FIG. 3) employing a shaft 31, a pair of linear actuators 41a and 41b, an end-effector 51 and optional rotary actuator 61.

Referring to FIG. 3, shaft 31 is structurally designed as a rigid or a semi-rigid shaft having a hollow central core 32 for passing an interventional tool through shaft 31 to end-effector 51, and further having one or more lumens 33a and 33b for passing electrical wiring through shaft 31 to linear actuators 41 to be housed within slots 34a and 34b.

End-effector 51 is shaped and dimensioned as a cylinder for passively guiding or actively steering a positioning of the interventional tool within the anatomical object. In practice, end-effector 51 may be composed of echogenic material as known in the art for ultrasound imaging purposes and/or an imaging agent as known in the art for X-ray imaging purposes.

Alternatively to end-effector 51, an end-effector 52 is shaped and dimensioned as a plate for actively steering a positioning of the interventional tool within the anatomical object. In practice, end-effector 52 may also be composed of echogenic material as known in the art for ultrasound imaging purposes and/or an imaging agent as known in the art for X-ray imaging purposes.

Each linear actuator 41 includes a motor 42 for translating a rod 43 in a forward direction F or a reverse direction R. Each linear actuator 41a further includes a motor controller 44 for controlling motor 42. In practice, motor 42 may be electric (DC, brushless DC, AC), piezoelectric or pneumatic.

Additionally, a linear slider 45 or a post 48 may be substituted for one of the linear actuators 41.

Linear slider 45 may include a telescoping elements 46 and 47, or a pneumatic or spring base 47 for translating a rod 46 in a forward direction F or a reverse direction R in dependence upon a degree of downward pressure applied to rod 46.

Post 48 serves as a fulcrum about which an end-effector 51 pivots and/or rotates relative to shaft 31.

If employed, rotary actuator 61 includes a motor 62 for rotating a rod 63 in a clockwise direction C or a counter clockwise direction CW. A platform 65 is geared to rod 63 to thereby rotate in sync with rod 63. Rotary actuator 61 further includes a motor controller 64 for respectively controlling motor 42. In practice, motor 62 may be electric (DC, brushless DC, AC), piezoelectric or pneumatic.

Figure 5:
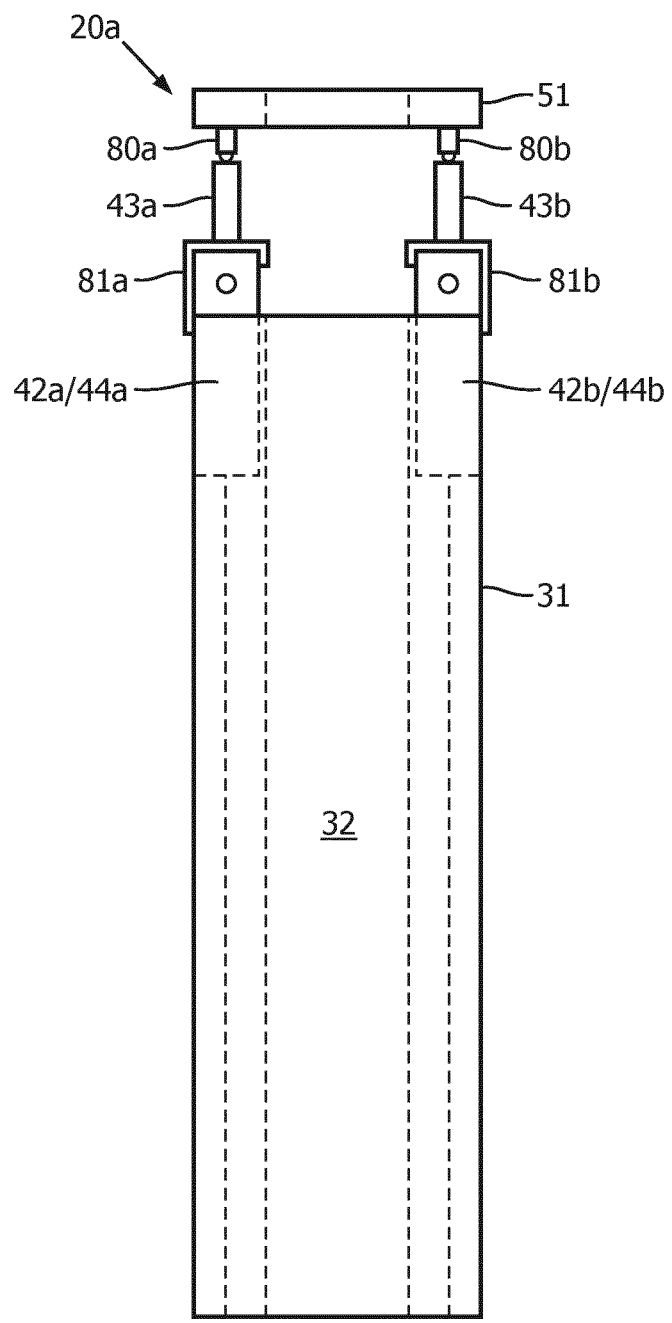
FIG. 5 illustrates an exemplary assembled embodiment of the steerable introducer shown in FIG. 3 in accordance with the inventive principles of the present disclosure.

FIG. 5 shows an assembled view of steerable introducer 20 (FIG. 3) employing shaft 31, linear actuators 41a and 41b, and an end-effector 51.

Referring to FIG. 5, motor 42a and motor controller 44a of linear actuator 41a are housed within shaft 31 and motor 42a is rigidly coupled to shaft 31 via a rotary joint 81a. Rod 43a extends from shaft 31 and is rotatably coupled to end-effector 51 via a rotary joint 80a.

Similarly, motor 42b and motor controller 44b of linear actuator 41b are housed within shaft 31 and motor 42b is rigidly coupled to shaft 31 via a rotary joint 81b. Rod 43b extends from shaft 31 and is rotatably coupled to end-effector 51 via a rotary joint 80b.

Figure 6A:
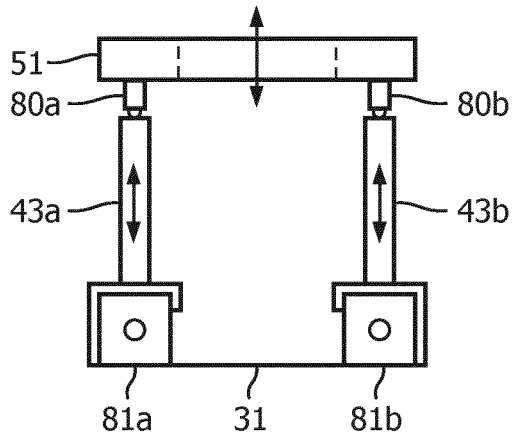
FIGS. 6A-6E illustrate exemplary motions of the steerable introducer shown in FIG. 5 in accordance with the inventive principles of the present disclosure.

As shown in FIG. 6A, a translation of rods 43a and 43b in a forward direction or a reverse direction translates end-effector 51 relative to shaft 31.

Figure 6D:
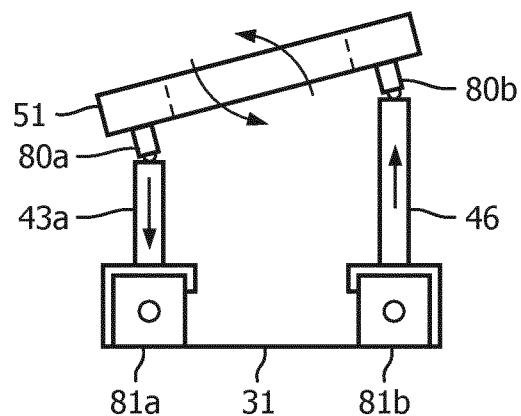
Figure 6B:
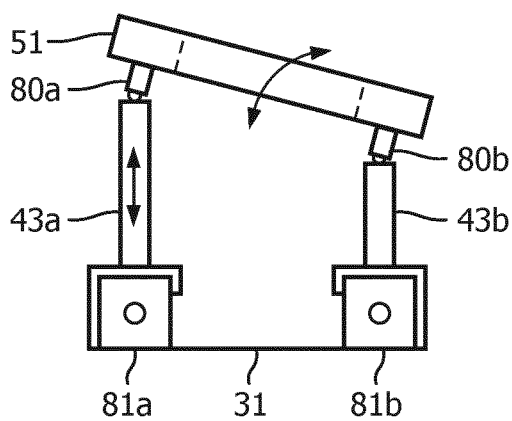

As shown in FIG. 6B, an exclusive translation of rod 43a in a forward direction or a reverse direction pivots end-effector 51 relative to shaft 31. Similarly, an exclusive translation of rod 43b in a forward direction or a reverse direction counter pivots end-effector 51 relative to shaft 31.

Figure 6E:
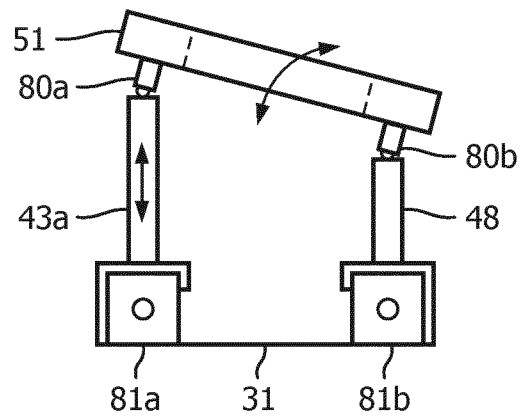
Figure 6C:
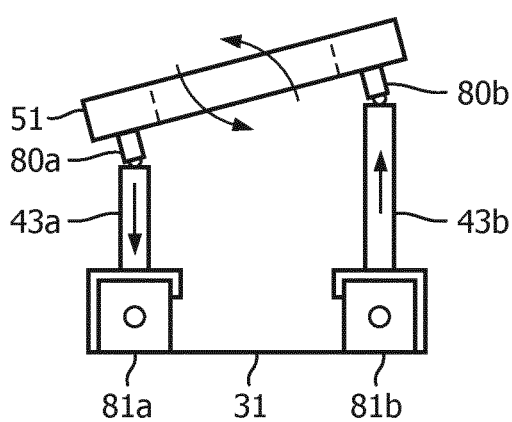

As shown in FIG. 6C, a translation of rod 43a in a reverse direction and a translation of rod 43b in a forward direction rotates end-effector 51 relative to shaft 31. Conversely, a translation of rod 43a in the forward direction and a translation of rod 43b in the reverse direction counter rotates end-effector 51 relative to shaft 31.

As shown in FIG. 6D, with linear slider 45 substituted for linear actuator 41b, a translation of rod 43a in a forward direction or a reverse direction rotates end-effector 51 relative to shaft 31.

As shown in FIG. 6E, with post 48 substituted for linear actuator 41b, a translation of rod 43a in a forward direction or a reverse direction pivots end-effector 51 relative to shaft 31.

In practice, those having ordinary skill in the art will appreciate the controllable translation, pivoting and rotating of end-effector 51 as shown in FIGS. 6A-6E provides for a translation motion and a pitch motion of end-effector 51.

Also in practice, additional linear actuators 41 employed motion coupler 40 provides for a yam motion of end-effector 51.

Figure 7A:
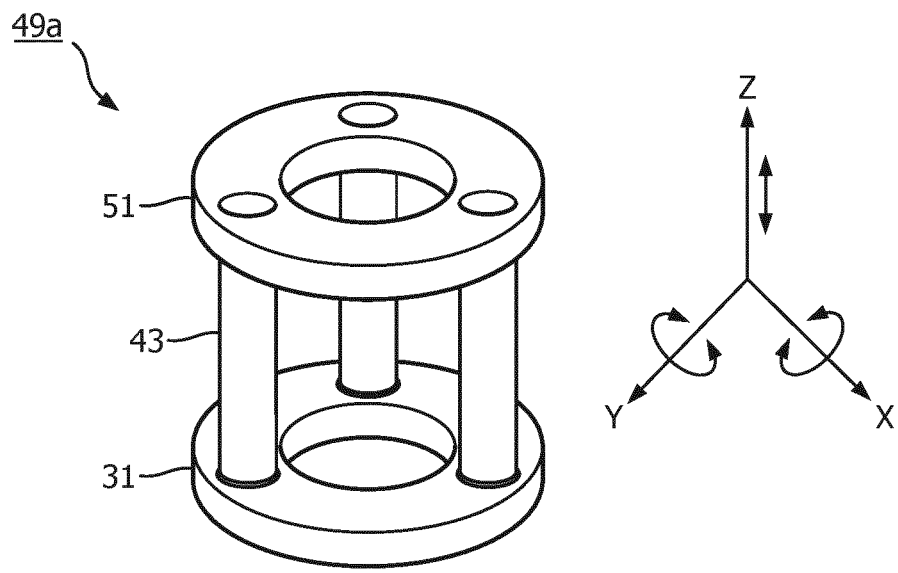
FIGS. 7A and 7B illustrate additional exemplary embodiments of linear actuator platforms in accordance with the inventive principles of the present disclosure.

For example, FIG. 7A illustrates a linear actuator platform 49a of three (3) linear actuators 43. The three (3) linear actuators 43 provide for a translation motion, a pitch motion and a yaw motion of end-effector 51 in three (3) degrees of freedom as shown.

Figure 7B:
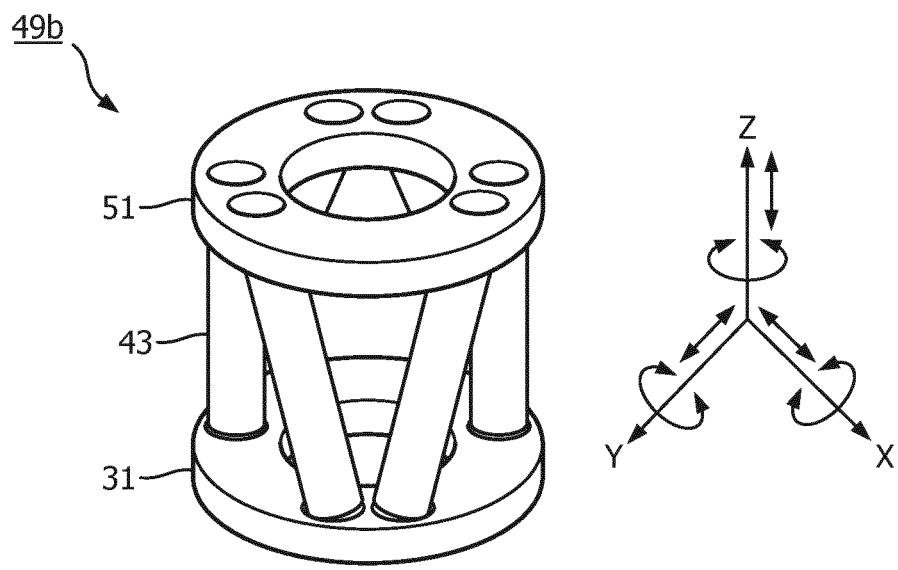

Also by example, FIG. 7B illustrates a Stewart platform 49b of six (6) linear actuators 43. The six (6) linear actuators 43 provide for a translation motion, a pitch motion and a yaw motion of end-effector 51 in six (6) degrees for freedom as shown.

In practice, as previously described herein, end-effector 51 may passively guide or actively steer a positioning of the interventional tool within the anatomical object.

Figure 8A:
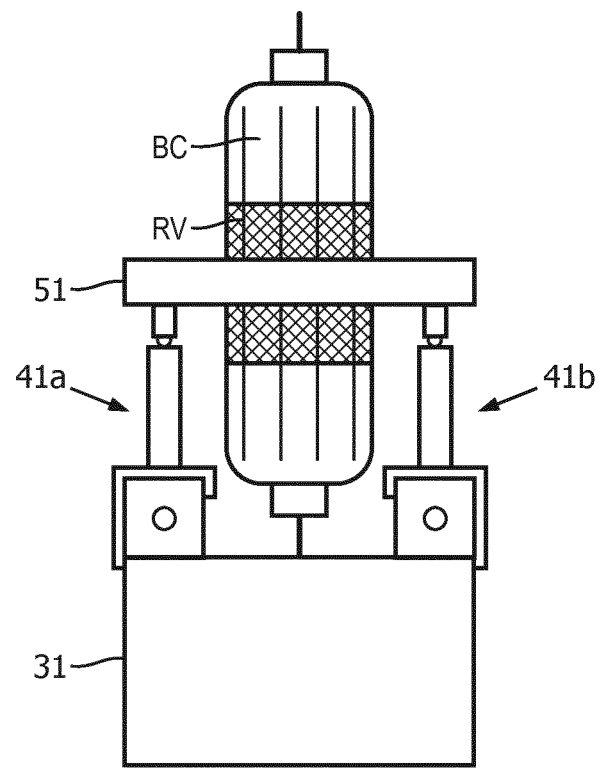
FIGS. 8A and 8B illustrates exemplary interactions between a balloon catheter and an end-effector in accordance with the inventive principles of the present disclosure.

For example, FIG. 8A illustrates a passage of a balloon catheter BC supporting a replacement aortic valve RV through shaft 31. Balloon catheter BC may be passively guided through end-effector 51 to a position within the anatomical object subsequent to a targeted positioning of end-effector 51 within the anatomical object, or alternatively may be separably adjoined to end-effector 51 whereby a targeted positioning of end-effector 51 within the anatomical object actively steers balloon catheter BC within the anatomical object to a coaxial alignment and a coplanar alignment with an aortic valve.

Figure 8B:
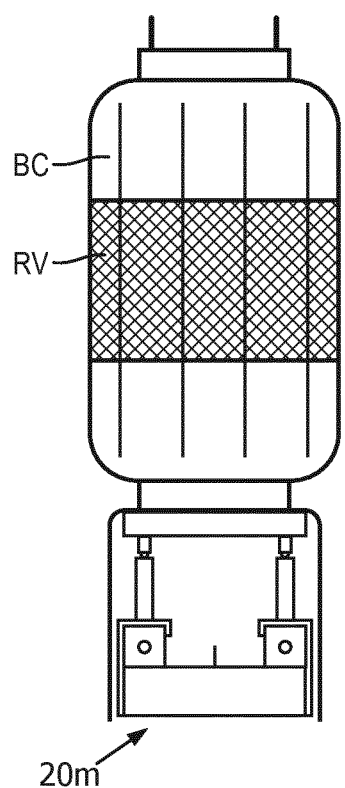

By further example, FIG. 8B illustrates a passage of balloon catheter BC supporting replacement aortic valve RV over shaft 31 for a miniaturized steerable introducer 20m. Balloon catheter BC is separably adjoined to end-effector 51 whereby a targeted positioning of end-effector 51 within the anatomical object actively steers balloon catheter BC within the anatomical object to a coaxial alignment and a coplanar alignment with an aortic valve.

In practice, as previously described herein, a rotary actuator may be employed with steerable introducer 20.

Figure 9A:
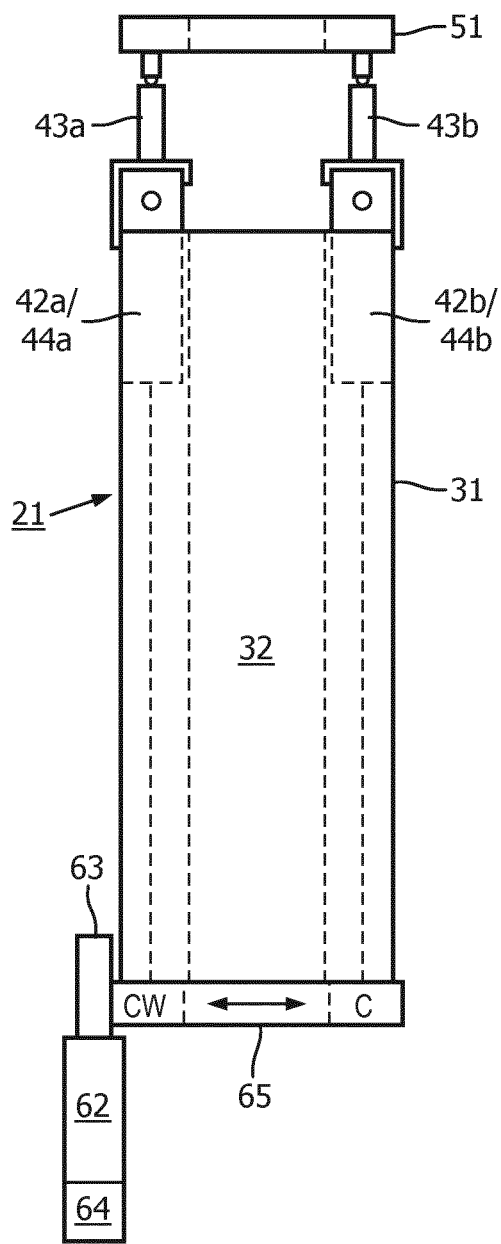
FIGS. 9A and 9B illustrate additional exemplary assembled embodiments of the steerable introducer shown in FIG. 3 in accordance with the inventive principles of the present disclosure.

For example, FIG. 9A illustrates an adjoining of a proximal end of shaft 31 of steerable introducer 20 to a cylindrical platform 66 of rotary actuator 61. Rotary rod 63 is controllable to actuate a rotation of end-effector 51 about a longitudinal axis of shaft 31.

Figure 9B:
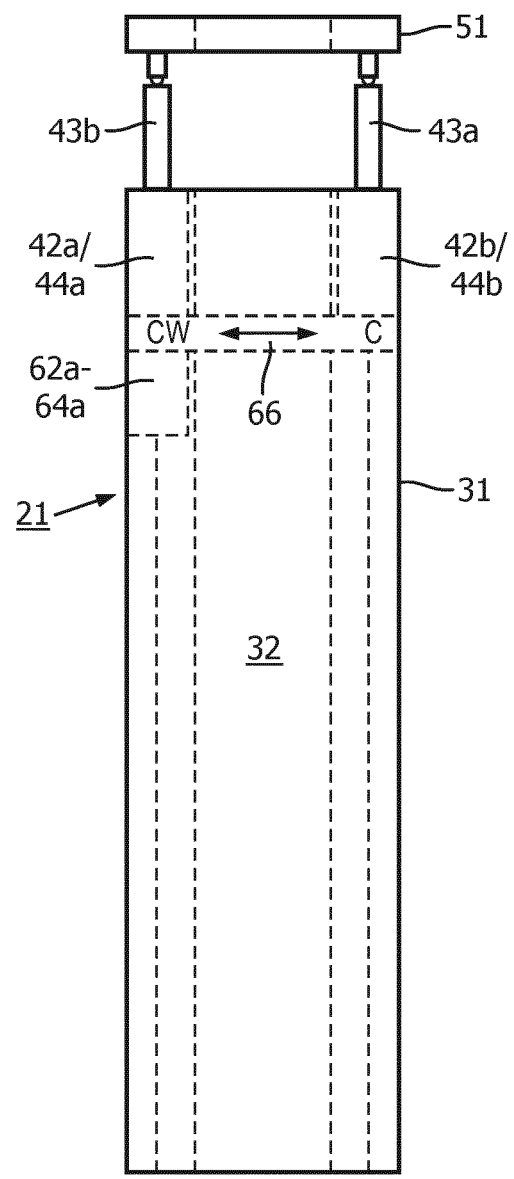

By further example, FIG. 9B illustrates a housing of rotary actuator 61 within shaft 31 with motors 42 and motor controllers 44 of linear actuators 41 being adjoined to cylindrical platform 66 of rotary actuator 61. Rod 63 is controllable to actuate a rotation of end-effector 51 about a longitudinal axis of end-effector 51.

Figure 10:
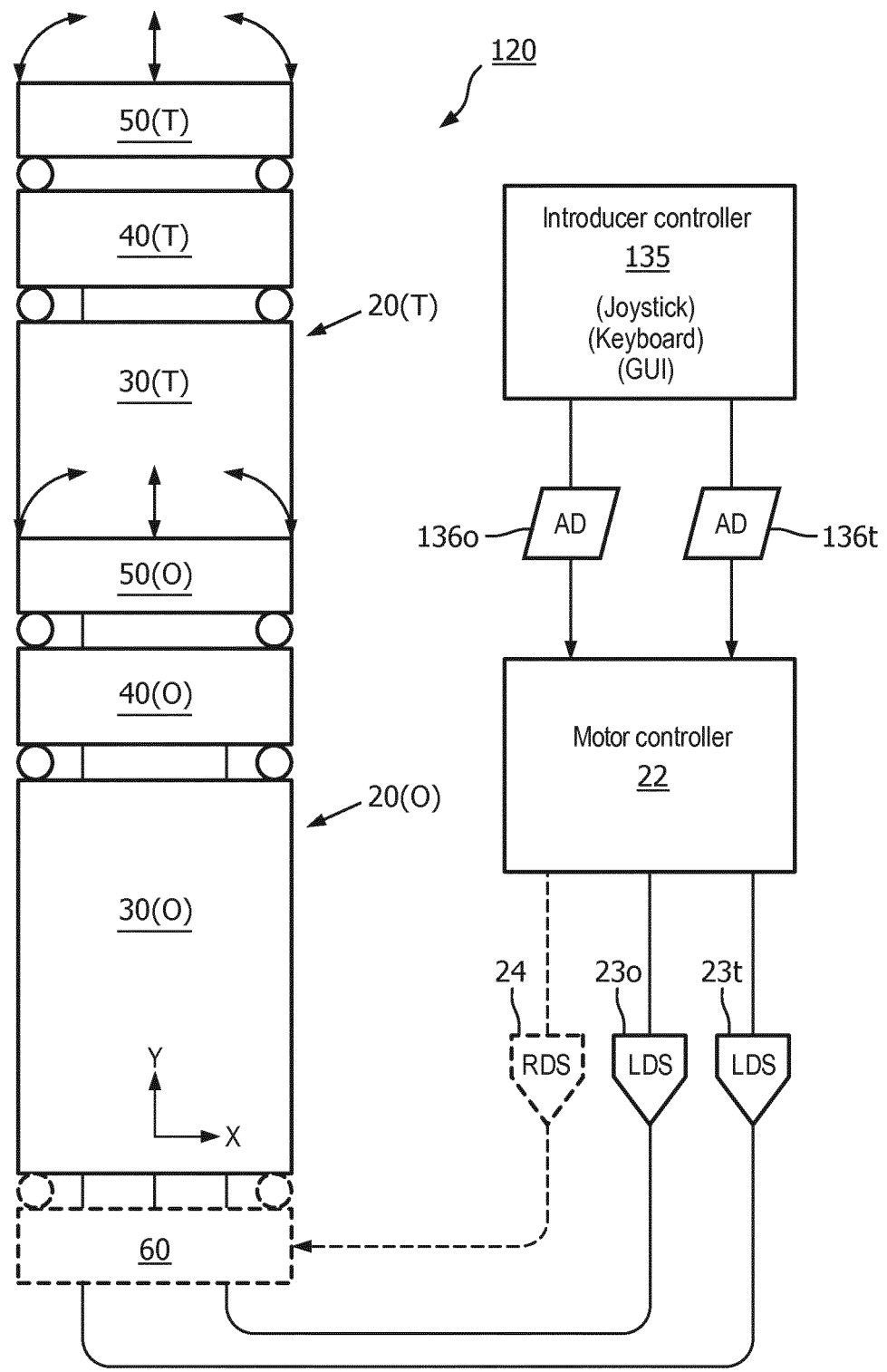
FIG. 10 illustrates an exemplary general embodiment of steerable introduction device in accordance with the inventive principles of the present disclosure.

To facilitate an understanding of the various inventions of the present disclosure, the following description of FIG. 10 teaches basic inventive principles of the present disclosure associated with a manufacture of a steerable introduction device of the present disclosure. From this description, those having ordinary skill in the art will appreciate how to apply the inventive principles of the present disclosure for making numerous and various embodiments of steerable introduction devices of the present disclosure. Please note the components of the present disclosure as shown in FIG. 10 are not drawn to scale, but drawn to conceptually visualize the inventive principles of the present disclosure.

Generally, a steerable introduction device of the present disclosure employs two (2) or more steerable introducers in a stacked arrangement. For a pair of adjacent steerable introducers, a shaft of one of the steerable introducers is adjoined to an end-effector of the other steerable introducer.

Referring to FIG. 10, a steerable introduction device 120 employs an orienting steerable introducer 20(O) and a translating steerable introducer 20(T) in a stacked arrangement involving an adjoining of shaft 30(T) of steerable introducer 20(T) to end-effector 50(O) of steerable introducer 20(O). For this embodiment, introducer controller 137 generates distinct respective actuation data 136o and 136t for sequentially or concurrently actuating motion coupler 40(O) and motion coupler 40(T).

In operation, the linear actuator(s) of motion coupler 40(O) is(are) controllable by an introducer controller 135 to actuate a translation, a pivoting and/or a rotation of end-effector 50(O) and end-effector 50(T) relative to shaft 30(O), and linear actuators 40(T) is(are) controllable by introducer controller 135 to actuate a translation, a pivoting and/or a rotation of end-effector 50(T) relative to shaft 30(T). In this context, the linear actuator(s) of motion coupler 40(O) may be exclusively utilized for orienting end-effector 50(T) and the linear actuator(s) of motion coupler 40(T) may be exclusively utilized for translating end-effector 50(T).

In practice, the adjoining of shaft 30(T) of steerable introducer 20 to end-effector 50(O) of steerable introducer 20 may be secured, or separable whereby the steerable introducers 20 may disjoined and used individually.

Further in practice, motor controller 22 may be external to steerable introducers 20(O) and 20(T) as shown, or alternatively as further described herein, each linear actuator of motion couplers 40(O) and 40(T), and rotary actuator 60 if applicable may employ an individual motor controller 22.

Figure 11:
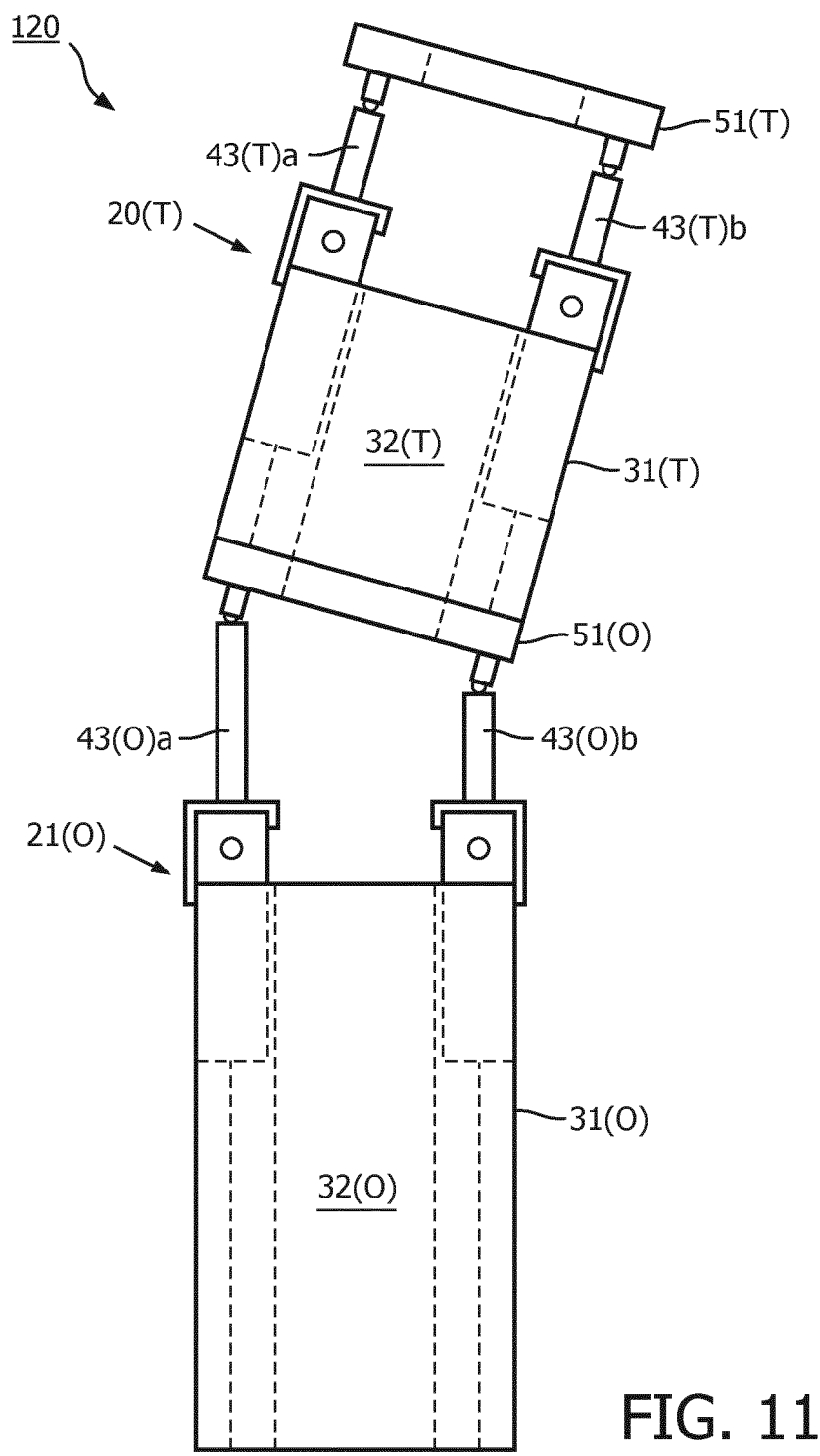
FIG. 11 illustrates an exemplary assembled embodiment of the steerable introducer shown in FIG. 10 in accordance with the inventive principles of the present disclosure.

FIG. 11 illustrates an embodiment of steerable introduction device 21 (FIG. 10) employing employs an orienting steerable introducer 20(O) and a translating steerable introducer 20(T) in a stacked arrangement involving an adjoining of shaft 31(T) of steerable introducer 20(T) to end-effector 51(O) of steerable introducer 20(O). In operation, rods 43a(O) and 43b(O) are controllable to actuate a translation, a pivoting and/or a rotation of end-effector 51(O) and end-effector 51(T) relative to shaft 31(O), and rods 43a(T) and 43b(T) are controllable to actuate a translation, a pivoting and/or a rotation of end-effector 51(T) relative to shaft 31(T). In this context, the linear actuator(s) of orienting steerable introducer 20(O) may be exclusively utilized for orienting end-effector 51(T), and the linear actuator(s) of translating steerable introducer 20(T) may be exclusively utilized for translating end-effector 50(T).

Figure 12:
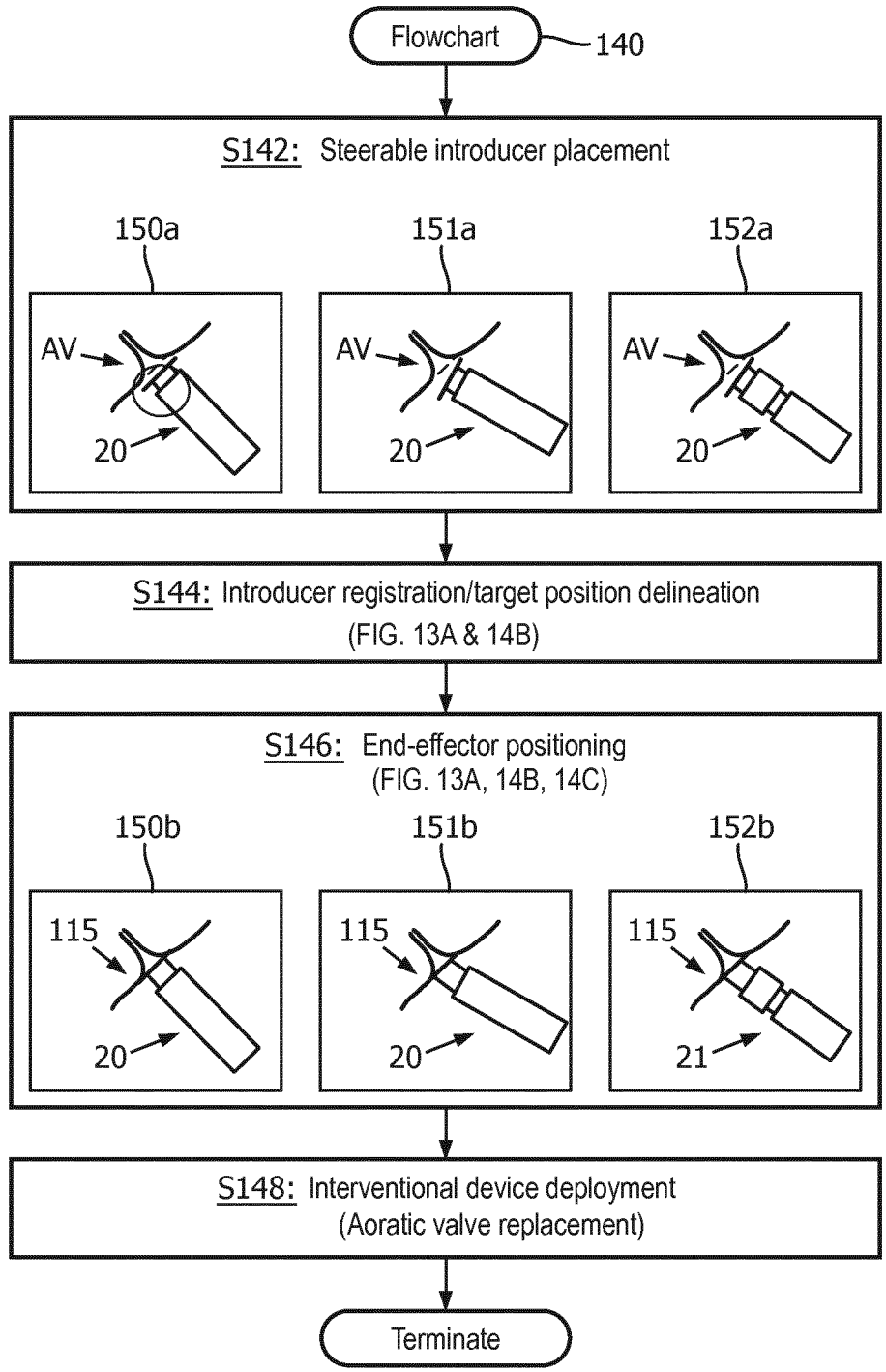
FIG. 12 illustrates a flowchart representative of an exemplary embodiment of an interventional method in accordance with the inventive principles of the present disclosure.

To facilitate a further understanding of the various inventions of the present disclosure, the following description of FIG. 12 teaches basic inventive principles associated with interventional methods of the present disclosure in the context of a minimally invasive aortic valve replacement. From this description, those having ordinary skill in the art will appreciate how to apply the inventive principles of the present disclosure for making and using additional embodiments of interventional methods of the present disclosure for any type of minimally invasive procedure suitable for a steerable introducer/introduction device of the present disclosure. Please note the components of the present disclosure as shown in FIG. 12 are not drawn to scale, but drawn to conceptually visualize the inventive principles of the present disclosure.

Referring to FIG. 12, a stage S142 of a flowchart 140 encompasses a user placement of steerable introducer 20 (FIG. 2) or steerable introduction device 21 (FIG. 2) into a heart of a patient as illustrated in a surgical image via fluoroscopic imager 100 (FIG. 2) encircling the thoracic cavity of the patient or via TEE probe 110 (FIG. 2) placed in the esophagus of the patient.

A transapical approach of stage S142 involves a small incision in a lower part of a chest, and a small puncture in left ventricle of the beating heart. The placement of steerable introducer 20 or of steerable introduction device 21 into the heart may position an end-effector of steerable introducer 20 or of steerable introduction device 21 anywhere within the left ventricle as illustrated in the surgical image via fluoroscopic imager 100 or TEE probe 110.

For example, a scenario 150*a* is an exemplary coaxial alignment and coplanar misalignment of an end-effector of steerable introducer 20 with an aortic valve AV of the heart.

By further example, a scenario 151*a* is an exemplary coaxial misalignment and coplanar misalignment of an end-effector of steerable introducer 20 with an aortic valve AV of the heart.

By further example, a scenario 152*a* is an exemplary coaxial misalignment and coplanar misalignment of an end-effector of steerable introduction device 21 with an aortic valve AV of the heart.

A transaortic approach of stage S142 involves a small incision in an upper part of a chest of the patient, and a small puncture in the aorta of the beating heart of the patient. The placement of steerable introducer 20 or of steerable introduction device 21 into the heart may position (i.e., location and orientation) an end-effector of steerable introducer 20 or of steerable introduction device 21 anywhere within the aorta as illustrated in the surgical image via TEE probe 110 or alternatively fluoroscopic imager 100.

Those having skill in the art will appreciate exemplary transapical scenarios of the transaortic approach analogous to the scenarios 150*a*-152*a*.

A stage S144 of flowchart 140 encompasses image controller 134 (FIG. 2) facilitating a registration of steerable introducer 20 or of steerable introduction device 21 to the applicable imaging modality, fluoroscopic imager 100 or TEE probe 110.

In practice, the registration may be executed by any known technique in the art for generating a transformation matrix between an actuation coordinate system of steerable introducer 20 or of steerable introduction device 21 to an image coordinate system of the applicable imaging modality.

The actuation coordinate system of steerable introducer 20 or of steerable introduction device 21 defines a reference point for tracking a position of the end-effector of steerable introducer 20 or of steerable introduction device 21 within the actuation coordinate system, particularly in terms of a location of specified point of the end-effector (e.g., a central point) and the orientation of the end-effector about the location of the specified point of the end-effector.

The image coordinate system of the applicable imaging modality defines a reference point for identifying positions of anatomical structures and of steerable introducer 20 or of steerable introduction device 21 within the live images of the anatomical object.

Also in practice, the actuation coordinate system of steerable introducer 20 or of steerable introduction device 21 is assumed to be static in view of a shaft of steerable introducer 20 or of steerable introduction device 21 being anchored in a heart muscle. By comparison, the image coordinate system may be static in view of a fixed positioning of the applicable imaging modality whereby the initial registration is maintained over an execution of flowchart 140. Conversely, the image coordinate system may be dynamic in view of a changing positioning of the applicable imaging modality whereby the initial registration is updated as needed over an execution of flowchart 140.

Stage S144 of flowchart 140 further encompasses image controller 134 facilitating a surgeon delineation or an image delineation of a target position of the end-effector of steerable introducer 20 or of steerable introduction device 21 within the live image of the anatomical object.

In one embodiment, a surgeon may outline a desired target position of the end-effector of steerable introducer 20 or of steerable introduction device 21 within the live image of the anatomical object.

In a second embodiment, image controller 134 performs an automatic segmentation of the targeted structure within the live image of the anatomical object as known in the art, and determines a desired target position of the end-effector of steerable introducer 20 or of steerable introduction device 21 relative to the segmented structure.

In practice, the delineated target position may be described as a plane defined by a center and a unit vector normal to the plane.

A stage S146 of flowchart 140 encompasses an actuation of steerable introducer 20 or of steerable introduction device 21 by introducer controller 135 for steering the end-effector thereof to the delineated target position for achieving a coaxial alignment and/or a coplanar alignment of the end-effector of steerable introducer 20 or of steerable introduction device 21 with an aortic valve AV of the heart as shown in live images of the heart (e.g., X-ray or ultrasound).

For example, a scenario 150*b* is an exemplary translation motion of the end-effector to thereby achieve a coaxial alignment and a coplanar alignment of an end-effector of a steerable introducer 20 with an aortic valve AV of the heart.

By further example, a scenario 151*b* is an exemplary translation motion and pitch motion of the end-effector to thereby achieve a coaxial alignment and a coplanar alignment of an end-effector of steerable introducer 20 with aortic valve AV of the heart.

By further example, a scenario 152*b* is an exemplary translation motion and pitch motion of the end-effector to thereby achieve a coaxial alignment and a coplanar alignment of an end-effector of steerable introduction device 21 with aortic valve AV of the heart.

Those having skill in the art will appreciate exemplary scenarios of the transaortic approach analogous to the transapical scenarios 150*b*-152*b*.

A stage S148 of flowchart 140 encompasses a deployment of an artificial valve by passing a balloon catheter supporting the artificial valve through steerable introducer 20 or steerable introduction device 21 and the end-effector thereof guiding a positioning of a balloon catheter supporting an artificial valve. Alternatively, the balloon catheter may be securely or separably adjoined to the end-effector of steerable introducer 20 or of steerable introduction device 21 during stages S142 and S144 whereby introducer controller 135 via the live image identifies and accounts for the balloon catheter during the placement of steerable introducer 20 or of steerable introduction device 21 of stage S142 and the positioning of the end-effector during stage S146.

Flowchart chart 140 is terminated upon deployment of the artificial valve.

To facilitate a further understanding of the various inventions of the present disclosure, the following description of FIGS. 13 and 14 teaches basic inventive principles associated with image registration, target position delineation and image guidance of an interventional method of the present disclosure. From this description, those having ordinary skill in the art will further appreciate how to apply the inventive principles of the present disclosure for making and using additional embodiments of interventional methods of the present disclosure for any type of minimally invasive procedure suitable for a steerable introducer/steerable introduction device of the present disclosure. Please note the components of the present disclosure as shown in FIGS. 13 and 14 are not drawn to scale, but drawn to conceptually visualize the inventive principles of the present disclosure.

Figure 13A:
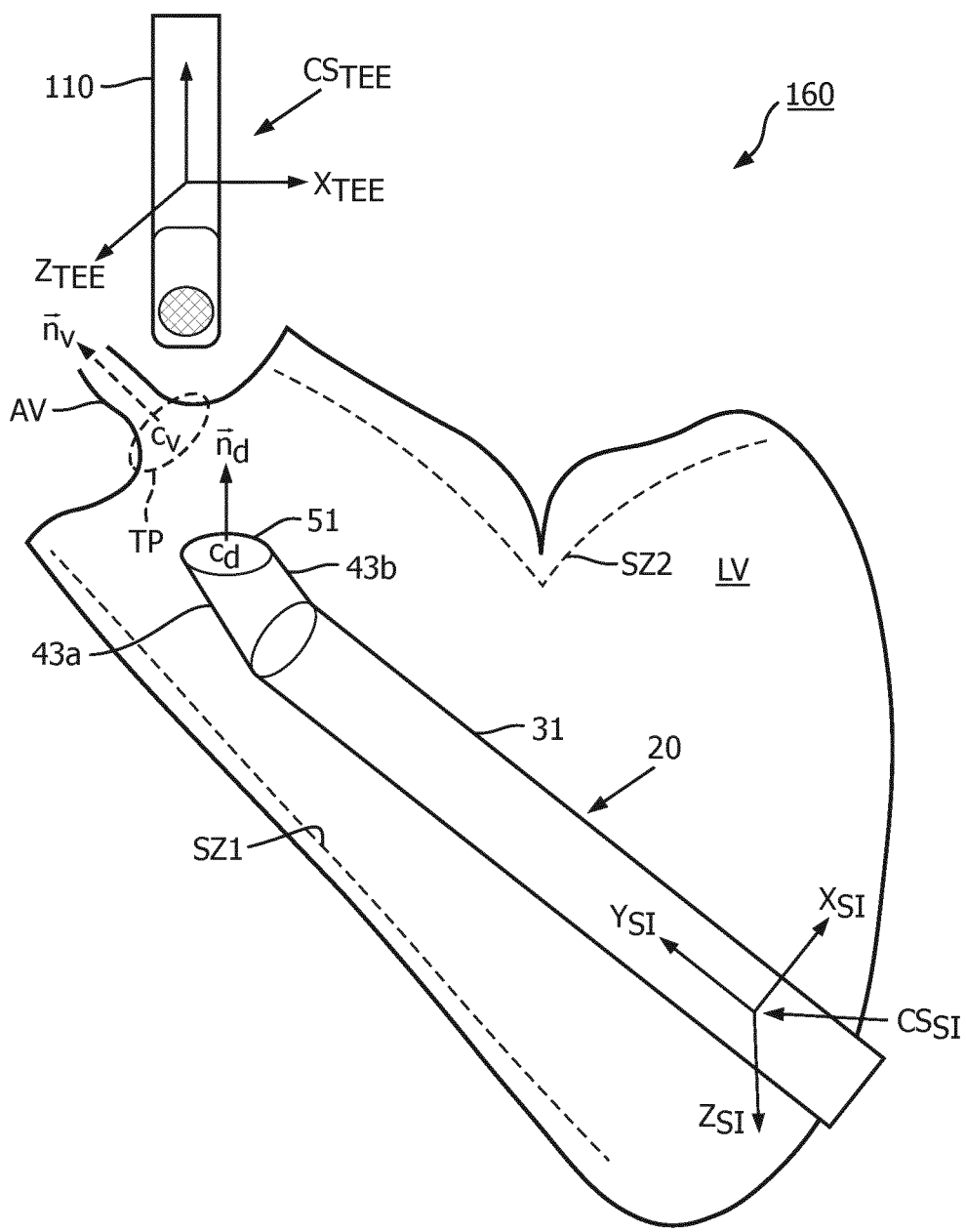
FIG. 13A illustrates an exemplary registration of a steerable introducer and a transesophageal echocardiogram (TEE) probe in accordance with the inventive principles of the present disclosure.

Referring to FIG. 13A, a transapical approach 160 involves a placement of steerable introducer 20 within left ventricle LV of a heart whereby steerable introducer 20 is anchored in the heart muscle to define an actuation coordinate system $CS_{SI}$. TEE probe 110 is positioned within an esophagus (not shown) to image end-effector 51 of steerable introducer 20 relative to aortic valve AV of the heart. TEE probe 110 has an imaging coordinate system $CS_{TEE}$ that may be static whereby a single registration between the coordinate systems $CS_{SI}/CS_{TEE}$ is required, or dynamic whereby the registration between the coordinate systems $CS_{SI}/CS_{TEE}$ is sporadically or continually updated.

Transapical approach 160 further involves a delineation of a target position TP described as a plane defined by a center $c_v$ denoting a target location of end-effector 51 within the registered imaging coordinate system $CS_{TEE}$, and a unit vector $\vec{n}_v$ normal to the plane denoting a target orientation of end-effector 51 within the registered imaging coordinate system $CS_{TEE}$.

Optionally, one or more safe zones may be delineated within left ventricle LV. For example, adherence to a safe zone SZ1 impedes any potential damage to an interventricular septum of the heart and adherence to a safe zone SZ2 impedes any potential damage to a mitral valve of the heart.

Figure 13B:
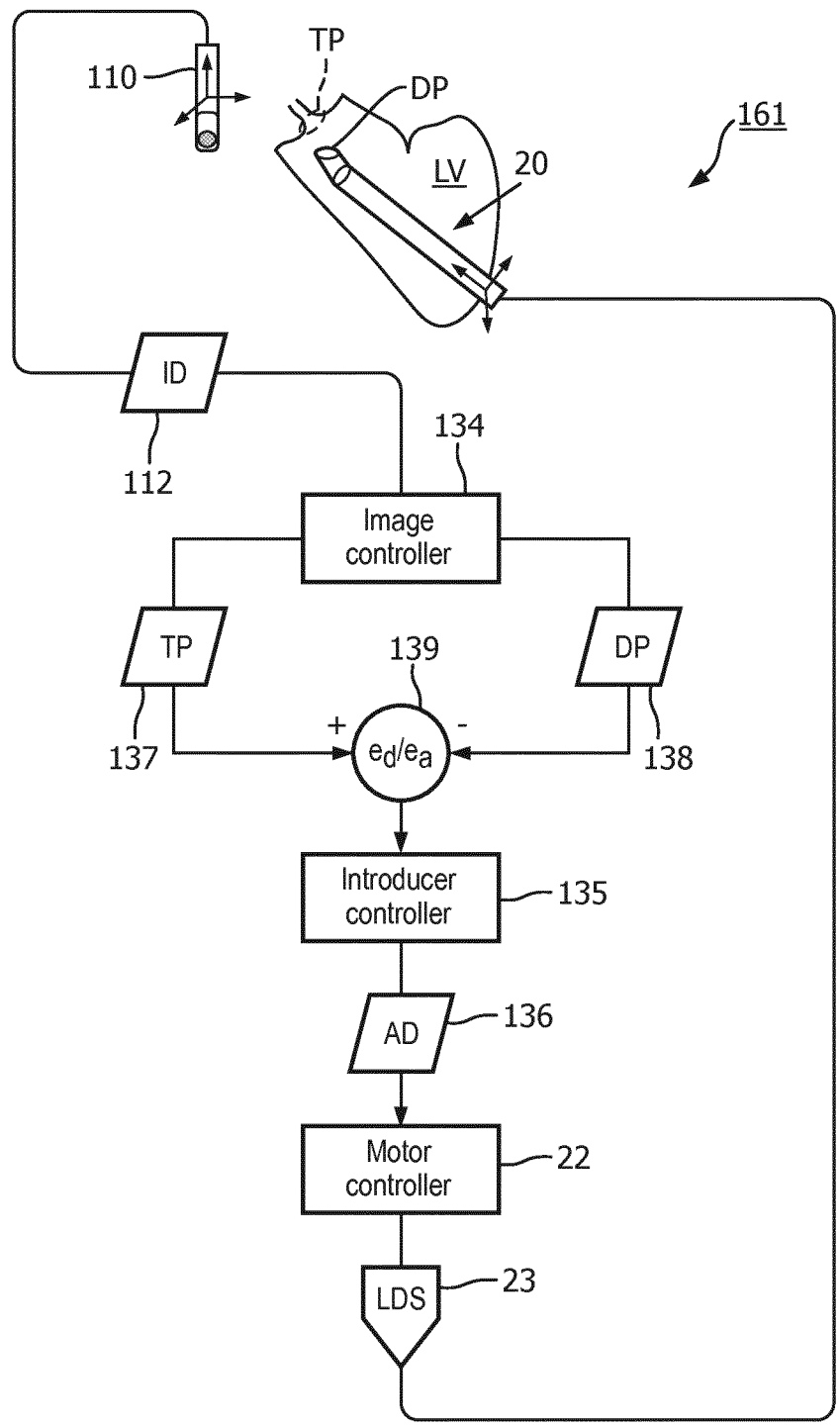
FIG. 13B illustrates an exemplary control loop of the registered steerable introducer and TEE probe of FIG. 13A in accordance with the inventive principles of the present disclosure.

Referring to FIGS. 13A and 13B, a control loop 161 for the transapical approach 160 of FIG. 13A is based on a positioning error differential between a delineation of a target position of the end-effector within the anatomical object as illustrated by the surgical image data and an identification of the position of the end-effector within the anatomical object as illustrated by the surgical image data.

Specifically, control loop 161 includes image controller 134 processing ultrasound image data 112 for the delineation of a target position 137 within the live ultrasound image in accordance with stage S144 (FIG. 12) and for subsequently detecting a device position 138 of end-effector 51 within the live ultrasound image in accordance with stage S146 (FIG. 12).

Control loop 161 further includes a digital subtractor 139 for ascertaining a position distance error signal $e_d$ as a dot differential between the center $c_v$ of the target position and the center $c_d$ of the end-effector in accordance with the following equation [1]:

$$e_d = \|c_v - c_d\| \quad [1]$$

Digital subtractor 139 further generates an alignment error signal $e_a$ as a dot product of two planes normal indicative of an angular error in accordance with the following equation [2]:

$$e_a = \vec{n}_v \cdot \vec{n}_d \quad [2]$$

An additional digital subtractor (not shown) may be included to generate a safety error signal $e_s$ as a dot differential between the center $c_v$ of the detected end-effector 51 and a spot location $c_s$ of the anatomical object closest to end-effector 51 in accordance with the following equation [3]:

$$e_d = \|c_s - c_d\| \quad [3]$$

Control loop 161 further includes introducer controller 135 processing the applicable error signals as inputs to an inverse kinematics computation of image registered steerable introducer 20 to ascertain required linear motion(s) of linear actuator(s) 43 of steerable introducer 20. Actuation data 136 informative of such linear motion(s) is communicated from introducer controller 135 to motor controller 22, which in turns applies linear drive signals 23 to linear actuator(s) 43 of the steerable introducer 20 to actuate the necessary motion of end-effector 51 to target position TP.

Control loop 161 is cyclical until such time end-effector 51 reaches target position TP. Those having ordinary skill in the art will appreciate a transaortic approach of control loop 161.

Figure 14A:
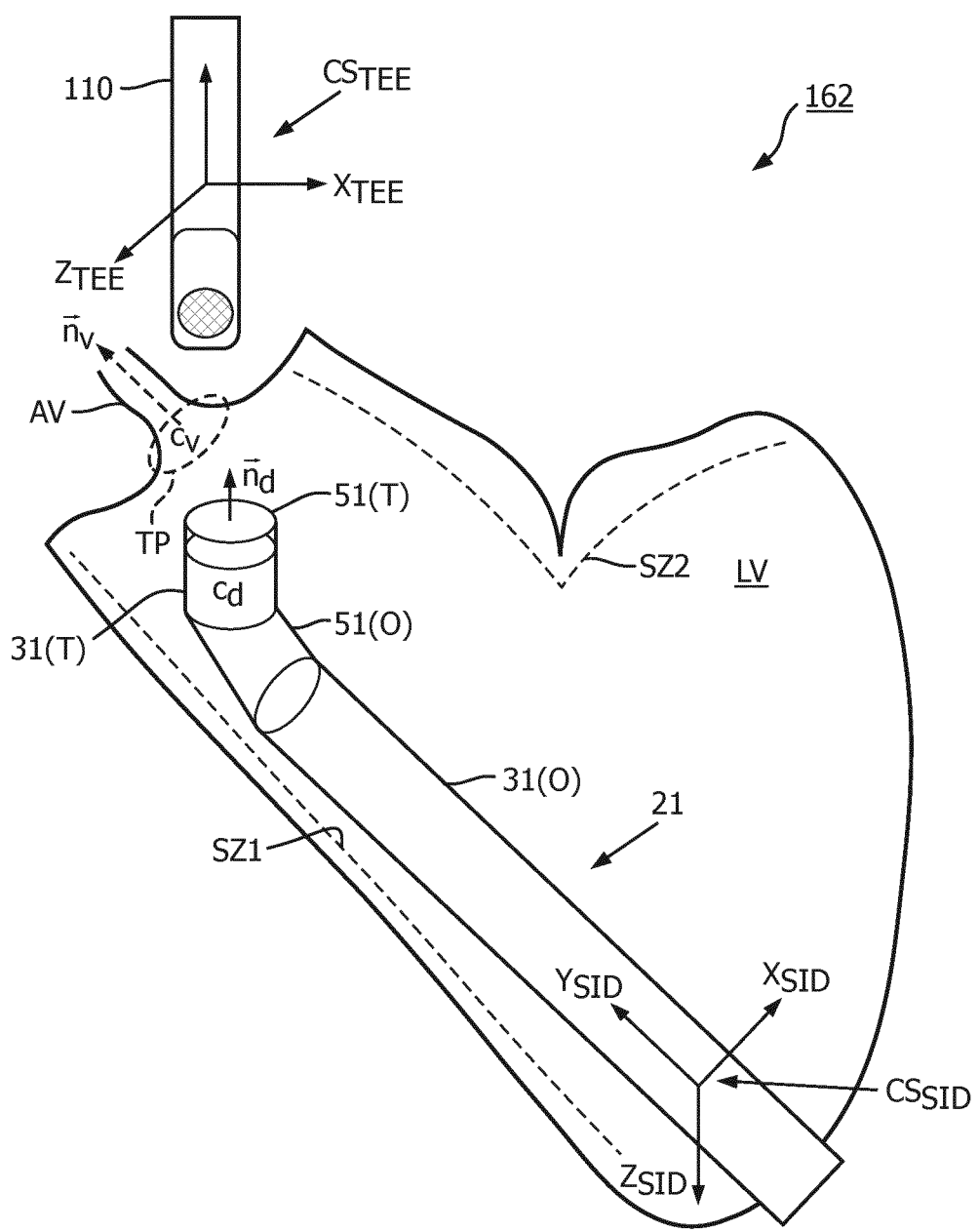
FIG. 14A illustrates an exemplary registration of a steerable introduction device and a transesophageal echocardiogram (TEE) probe in accordance with the inventive principles of the present disclosure.

Referring to FIG. 14A, a transapical approach 162 involves a placement of steerable introduction device 21 within left ventricle LV of a heart whereby steerable introduction device 21 is anchored in the heart muscle to define an actuation coordinate system $CS_{SID}$. As previously described, TEE probe 110 is positioned within an esophagus (not shown) to image end-effector 51(T) of steerable introduction device 21 relative to aortic valve AV of the heart. TEE probe 110 as an imaging coordinate system $CS_{TEE}$ that may be static whereby a single registration between the coordinate systems is required, or dynamic whereby the registration between the coordinate systems is sporadically or continually updated.

Transapical approach 162 further involves a delineation of a target position TP described as a plane defined by a center $c_v$ denoting a target location of end-effector 51(T) within the registered imaging coordinate system $CS_{TEE}$, and a unit vector $\vec{n}_v$ normal to the plane denoting a target orientation of end-effector 51(T) within the registered imaging coordinate system $CS_{TEE}$.

As previously described, one or more safe zones may be delineated within left ventricle LV. For example, adherence to a safe zone SZ1 impedes any potential damage to an interventricular septum of the heart and adherence to a safe zone SZ2 impedes any potential damage to a mitral valve of the heart.

Figure 14B:
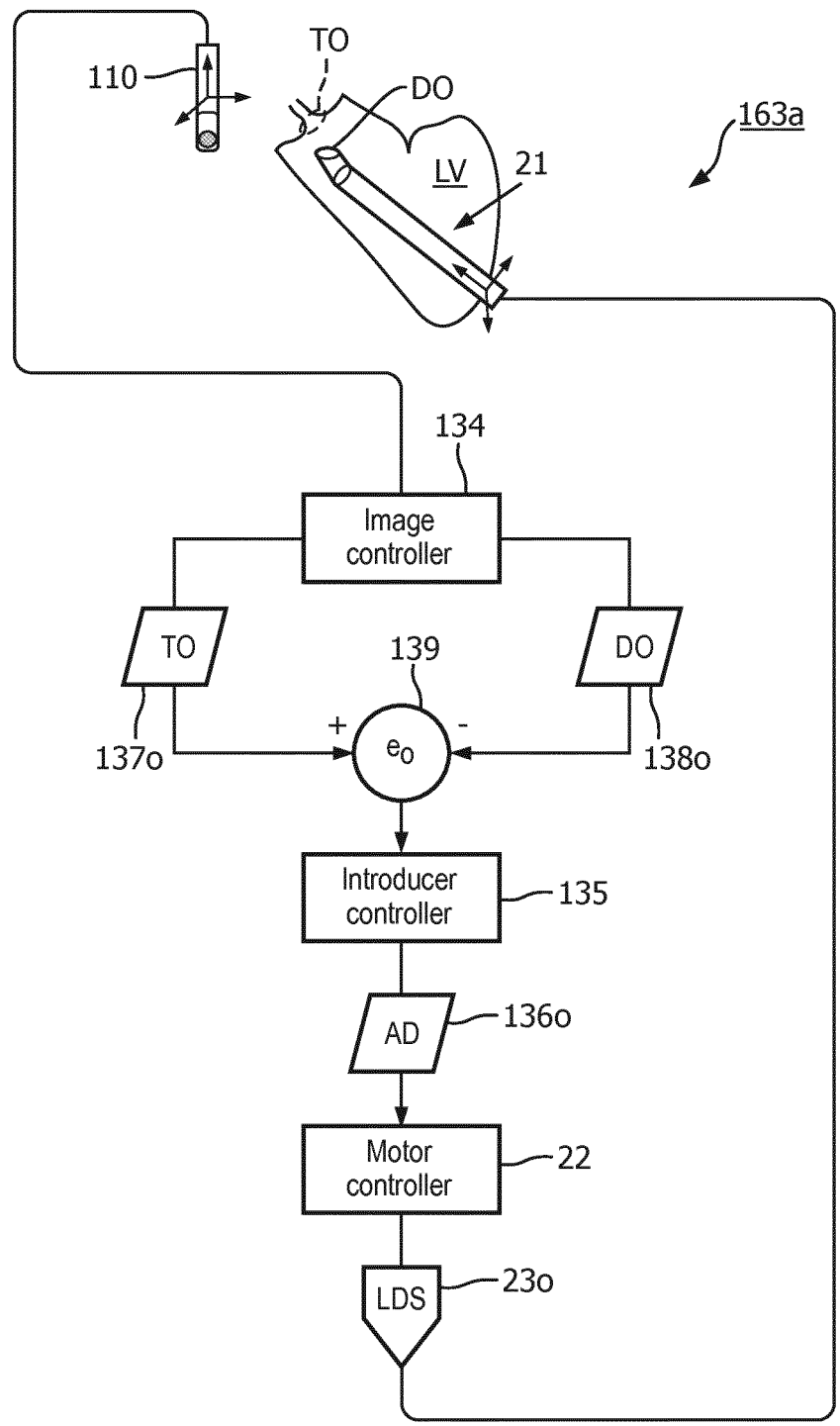
FIGS. 14B and 14C illustrate exemplary control loops of the registered steerable introduction device and TEE probe of FIG. 14A in accordance with the inventive principles of the present disclosure.

Referring to FIGS. 14A and 14B, a control loop 163a for the transapical approach 162 of FIG. 14A is based on an orientation error differential between a targeted orientation of the translating end-effector within the anatomical object and the surgical orientation of the translating end-effector within the anatomical object as illustrated by the surgical image data.

Specifically, control loop 163a includes image controller 134 processing ultrasound image data 112 for the delineation of a target orientation 137o within the live ultrasound image in accordance with stage S144 (FIG. 12) and for subsequently detecting a device orientation 138o of end-effector 51(T) within the live ultrasound image in accordance with stage S146 (FIG. 12).

Control loop 163a includes digital subtractor 139 generating an alignment error signal $e_a$ as a weighted dot product of two planes normal indicative of an angular error in accordance with the following equation [4]:

$$e_a = m \cdot \vec{n}_v \cdot \vec{n}_d \quad [4]$$

Control loop 163a further includes introducer controller 135 processing the alignment error signal as input to an inverse kinematics computation of image registered steerable introduction device 21 to ascertain required linear motion(s) of linear actuator(s) 43 of end-effector 51(O). Actuation data 136o informative of such linear motion(s) is communicated from introducer controller 135 to motor controller 22, which in turns applies linear drive signals 23o to linear actuator(s) 43 of the steerable introduction device 21 to actuate the necessary motion of end-effector 51(T) to target position TP.

Control loop 163a is cyclical until such time end-effector 51(T) reaches a target orientation of target position TP. Those having ordinary skill in the art will appreciate a transapical approach to control loop 163a.

Figure 14C:
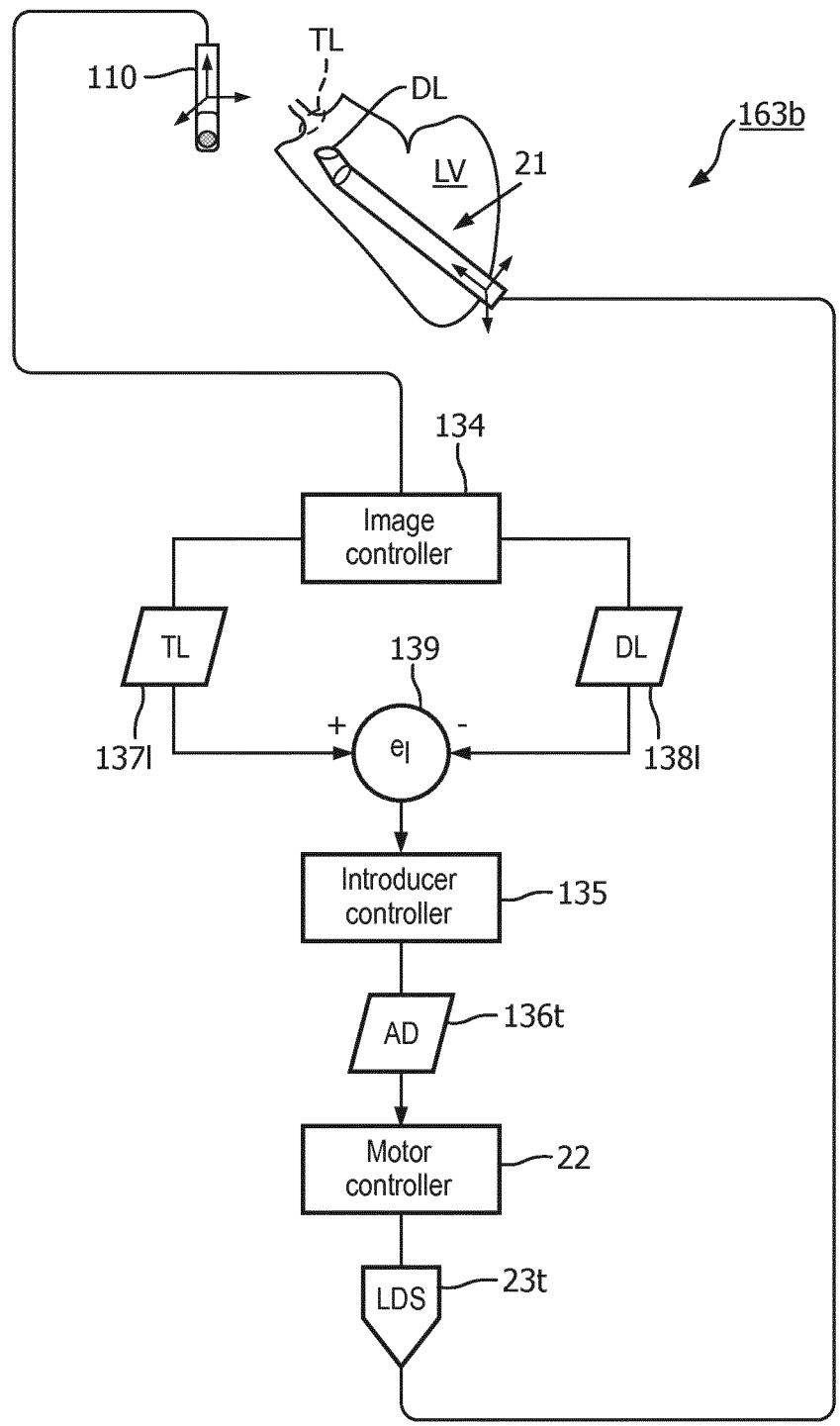

Referring to FIGS. 14A and 14C, a control loop 163b for the transapical approach 162 of FIG. 14A is based a location error differential between a targeted location of the translating end-effector within the anatomical object and the surgical location of the translating end-effector within the anatomical object as illustrated by the surgical image data.

Specifically, control loop 163b includes image controller 134 processing ultrasound image data 112 for the delineation of a target location 1371 within the live ultrasound image in accordance with stage S144 (FIG. 12) and for subsequently detecting a device location 1381 of end-effector 51(T) within the live ultrasound image in accordance with stage S146 (FIG. 12).

Control loop 161 further includes digital subtractor 139 for generating a weighted distance error signal $e_d$ as a dot differential between the center $c_v$ of the target position and the center $c_d$ of the end-effector in accordance with the following equation [5]:

$$e_d = n \cdot \|c_v - c_d\| \quad [5]$$

Control loop 163b further includes introducer controller 135 processing the distance error signal as an input to an inverse kinematics computation of image registered steerable introduction device 21 to ascertain required linear motion(s) of linear actuator(s) 43 of end-effector 51(T). Actuation data 136t informative of such linear motion(s) is communicated from introducer controller 135 to motor controller 22, which in turns applies linear drive signals 23f to linear actuator(s) 43 of the steerable introduction device 21 to actuate the necessary motion of end-effector 51(T) to a target location of target position TP.

Control loop 163b is cyclical until such time end-effector 51(T) reaches a target location of target position TP. Those having ordinary skill in the art will appreciate a transapical approach to control loop 163b.

Referring to FIGS. 1-14C, those having ordinary skill in the art will appreciate numerous benefits of the inventions of the present disclosure including, but not limited to, image guidance for a precise coaxial alignment and/or a precise coplanar alignment of an interventional tool as needed with a structure of an anatomical object in support of a deployment of the interventional tool during a minimally invasive procedure.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of novel and inventive image guidance of steerable introducers, and systems and methods incorporating such image guidance of steerable introducers, (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A steerable introduction system for deploying an interventional tool within an anatomical object, the steerable introduction system comprising:
 a steerable introducer including a motion coupler coupling an end-effector to a shaft for positioning the interventional tool within the anatomical object,
  wherein the shaft is configured to introduce the interventional tool into the anatomical object,
  wherein the end-effector is configured to interact with the interventional tool within the anatomical object, and
  wherein the motion coupler is configured to actuate at least one of a translation, a pivoting and a rotation of the end-effector relative to the shaft within the anatomical object; and
 an image guidance workstation,
  wherein the image guidance workstation in communication with the steerable introducer controls an actuation of the at least one of the translation, the pivoting and the rotation of the end-effector within the anatomical object responsive to surgical image data illustrative of a position of the end-effector within the anatomical object, wherein the motion couple includes at least one linear actuator controllable by the image guidance workstation to actuate the at least one of the translation, the pivoting and the rotation of the end-effector relative to the shaft within the anatomical object.

2. The steerable introduction system of claim 1,
wherein the control by the image guidance workstation of the actuation by the motion coupler of the at least one of the translation, the pivoting and the rotation of the end-effector relative to the shaft within the anatomical object is derived from a positioning error differential between a delineation of a target position of the end-effector within the anatomical object as illustrated by the surgical image data and an identification of the position of the end-effector within the anatomical object as illustrated by the surgical image data.

3. The steerable introduction system of claim 2,
wherein the image guidance workstation in communication with an imaging modality is further configured to at least one of: (1) control a delineation of the target position of the end-effector within the anatomical object as illustrated within the surgical image data, and (2) control an identification of a surgical position of the end-effector within the anatomical object as illustrated by the surgical image data.

4. The steerable introduction system of claim 2,
wherein the control by the image guidance workstation of the actuation by the motion coupler of the least one of the translation, the pivoting and the rotation of the end-effector relative to the shaft within the anatomical object is derived from a safe zone between the identification of the position of the end-effector within the anatomical object as illustrated by the surgical image data and an identification of an anatomical position of a sensitive structure of the anatomical object as illustrated by the surgical image data.

5. The steerable introduction system of claim 4,
wherein the image guidance workstation in communication with an imaging modality is further configured to at least one of control an identification of the position of the end-effector within the anatomical object as illustrated by the surgical image data and control an identification of the anatomical position of the sensitive structure of the anatomical object as illustrated by the surgical image data.

6. The steerable introduction system of claim 1, wherein the motion coupler further includes:
at least one linear slider translatable between the shaft and the end-effector responsive to an actuation by the image guidance workstation of the at least one linear actuator.

7. The steerable introduction system of claim 1, wherein the motion coupler further includes:
at least one post extending between the shaft and the end-effector.

8. The steerable introduction system of claim 1, wherein the motion coupler further includes:
a rotary actuator controllable by the imaging guidance workstation to actuate a rotation of the end-effector about a rotational axis of the end-effector.

9. The steerable introduction system of claim 1, further comprising:
a rotary actuator coupled to the shaft, wherein the imaging guidance workstation is further configured to control an actuation by the rotary actuator of a rotation of the shaft about a rotational axis of the shaft.

10. An interventional method incorporating a steerable introducer for positioning an interventional tool within an anatomical object,
the steerable introducer including a shaft positioned within the anatomical object to introduce the interventional tool into the anatomical object,
the steerable introducer further including an end-effector positioned within the anatomical object to interact with the interventional tool,
the steerable introducer further including a motion coupler positioned within the anatomical object to actuate at least one of a translation, a pivoting and a rotation of the end-effector relative to the shaft within the anatomical object, wherein the motion coupler includes at least one linear actuator, wherein the interventional method comprises:
an image guidance workstation receiving surgical image data illustrative of a position of the end-effector within the anatomical object;
the image guidance workstation steering the end-effector to a target position within the anatomical object responsive to the surgical image data; and
the image guidance workstation controlling the linear actuator of the motion coupler to actuate the at least one of the translation, the pivoting and the rotation of the end-effector relative to the shaft within the anatomical object.

11. The interventional method of claim 10, wherein the control by the image guidance workstation of the actuation by the motion coupler of the least one of the translation, the pivoting and the rotation of the end-effector within the anatomical object is derived from a positioning error differential between a delineation of the target position of the end-effector within the anatomical object as illustrated by the surgical image data and an identification of the position of the end-effector within the anatomical object as illustrated by the surgical image data.

12. The interventional method of claim 10, wherein the control by the image guidance workstation of the actuation by the motion coupler of the least one of the pivoting and the rotation of the end-effector within the anatomical object is derived from an orientation error differential between a targeted orientation of the end-effector within the anatomical object and an orientation of the end-effector within the anatomical object as illustrated by the surgical image data.

13. The interventional method of claim 10, wherein the control by the image guidance workstation of the actuation by motion coupler of the translation of the end-effector within the anatomical object is derived from a location error differential between a targeted location of the end-effector within the anatomical object and the location of the end-effector within the anatomical object as illustrated by the surgical image data.

14. The interventional method of claim 10,
wherein the control by the image guidance workstation of the actuation by the motion coupler of the least one of the translation, the pivoting and the rotation of the end-effector within the anatomical object is derived from a safe zone between an identification of the position of the end-effector within the anatomical object as illustrated by the surgical image data and an identification of an anatomical position of a sensitive structure of the anatomical object as illustrated by the surgical image data.

15. A steerable introduction system for deploying an interventional tool within an anatomical object, the steerable introduction system comprising:
a steerable introduction device including an orienting steerable introducer and a translating steerable introducer for positioning the interventional tool within the anatomical object; and
an image guidance workstation,
wherein the orienting steerable introducer includes:
a first shaft;
a first motion coupler; and
a first end-effector; and
wherein the first motion coupler is configured to couple the first shaft and the first end-effector;
wherein the translating steerable introducer includes:
a second shaft;
a second motion coupler; and
a second end-effector configured to interact with the interventional tool within the anatomical object;
wherein the second motion coupler is configured to couple the second shaft and the second end-effector; and
wherein the orienting steerable introducer and the translating steerable introducer are configured in a stacked arrangement such that the second shaft of the translating steerable introducer adjoins the first end-effector of the orienting steerable introducer;
wherein the image guidance workstation is in communication with the steerable introduction device and is configured to control:
a first actuation comprising at least one of translating, pivoting and rotating the first end-effector of the orienting steerable introducer within the anatomical object responsive to first surgical image data illustrative of a first surgical orientation of the first end-effector of the orienting steerable introducer within the anatomical object, and
a second actuation comprising at least one of translating, pivoting and rotation of the second end-effector of the translating steerable introducer within the anatomical object responsive to second surgical image data illustrative of a second surgical orientation of the second end-effector of the translating steerable introducer within the anatomical object;
wherein the first motion coupler of the orienting steerable introducer includes at least one first linear actuator controllable by the image guidance workstation to actuate the at least one of the translation, the pivoting and the rotation of the first end-effector of the orienting steerable introducer relative to the first shaft of the orienting steerable introducer; and
wherein the second motion coupler of the translating steerable introducer includes at least one second linear actuator controllable by the image guidance workstation to actuate the at least one of the translation, the pivoting and the rotation of the second end-effector of the translating steerable introducer relative to the second shaft of the translating steerable introducer.

16. The steerable introduction system of claim 15, wherein the first linear actuator of the first motion coupler is exclusively utilized for orienting the first end-effector and the second linear actuator of the second motion coupler is exclusively utilized for translating the second end-effector.

17. The steerable introduction system of claim 15, wherein the control by the image guidance workstation of the actuation of the at least one of the pivoting and the rotation of the first end-effector within the anatomical object is derived from an orientation error differential between a targeted orientation of the first end-effector within the anatomical object and the first surgical orientation of the first end-effector within the anatomical object as illustrated by the first surgical image data.

18. The steerable introduction system of claim 17, wherein the image guidance workstation is in communication with an image controller configured to at least one of:
i) delineate the target orientation of the first end-effector within the anatomical object as illustrated within the first surgical image data, and ii) identify the surgical orientation of the first end-effector within the anatomical object as illustrated by the first surgical image data.

19. The steerable introduction system of claim 15, wherein the control by the image guidance workstation of the actuation of the translation of the second end-effector within the anatomical object is derived from a location error differential between a targeted location of the second end-effector within the anatomical object and a surgical location of the second end-effector within the anatomical object as illustrated by the second surgical image data.

20. The steerable introduction system of claim 19, wherein the image guidance workstation is in communication with an image controller configured to at least one of:
(i) delineate the target location of the second end-effector within the anatomical object as illustrated within the second surgical image data, and (ii) identify a surgical location of the second end-effector within the anatomical object as illustrated by the second surgical image data.

* * * * *